(12) United States Patent
Chang et al.

(10) Patent No.: US 10,290,090 B2
(45) Date of Patent: May 14, 2019

(54) IMAGE-BASED TUBE SLOT CIRCLE DETECTION FOR A VISION SYSTEM

(71) Applicant: Siemens Healthcare Diagnostics Inc., Tarrytown, NY (US)

(72) Inventors: Yao-Jen Chang, Princeton, NJ (US); Wen Wu, Kirkland, WA (US); Guillaume Dumont, Paris (FR); Benjamin Pollack, Jersey City, NJ (US); Terrence Chen, Princeton, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 85 days.

(21) Appl. No.: 15/551,570

(22) PCT Filed: Feb. 16, 2016

(86) PCT No.: PCT/US2016/018109
§ 371 (c)(1),
(2) Date: Aug. 16, 2017

(87) PCT Pub. No.: WO2016/133924
PCT Pub. Date: Aug. 25, 2016

(65) Prior Publication Data
US 2018/0047150 A1 Feb. 15, 2018

Related U.S. Application Data

(60) Provisional application No. 62/117,914, filed on Feb. 18, 2015.

(51) Int. Cl.
*G06K 9/00* (2006.01)
*G06T 7/00* (2017.01)
(Continued)

(52) U.S. Cl.
CPC ........ *G06T 7/0004* (2013.01); *G06K 9/00208* (2013.01); *G06K 9/3233* (2013.01);
(Continued)

(58) Field of Classification Search
None
See application file for complete search history.

(56) References Cited

U.S. PATENT DOCUMENTS

| | | | |
|---|---|---|---|
| 8,854,451 B2* | 10/2014 | Cormier | G01N 17/02 148/518 |
| 2008/0044071 A1* | 2/2008 | Barbu | G06K 9/6256 382/128 |

(Continued)

FOREIGN PATENT DOCUMENTS

WO 2014/152329 A1 9/2014

OTHER PUBLICATIONS

Yuen H et al: "Comparative study of Hough Transform methods for circle finding", Image and Vision Computing, Elsevier, Guildford, GB, vol. 8, No. 1, Feb. 1, 1990 (Feb. 1, 1990), pp. 71-77, XP026655739, ISSN: 0262-8856, DOI: 10.1016/0262-8856 (90) 90059-E [retrieved on Feb. 1, 1990] *the whole document*.

(Continued)

*Primary Examiner* — Gandhi Thirugnanam

(57) ABSTRACT

Embodiments provide a method of using image-based tube top circle detection that includes extracting, from one of a series of images of a tube tray, a region of interest (ROI) patch having a target tube top circle and boundaries constrained by two dimensional (2D) projections of different types of tube top circle centers. The method also includes calculating an edge gradient magnitude map of the ROI patch and constructing a three dimensional (3D) map of a circle parameter space, each location in the 3D map corresponding to a circle parameter having a center location and (Continued)

a diameter. The method further includes accumulating weighted votes in the 3D map from edge points in the edge gradient magnitude map along edge point gradient directions, determining locations in the 3D map as circle candidates based on the accumulated votes and selecting a target tube top circle based on the greatest accumulated votes.

22 Claims, 18 Drawing Sheets

(51) Int. Cl.

| | |
|---|---|
| *G06T 7/12* | (2017.01) |
| *G06K 9/32* | (2006.01) |
| *G06K 9/46* | (2006.01) |
| *G06T 7/11* | (2017.01) |
| *G06T 7/13* | (2017.01) |
| *G06T 7/60* | (2017.01) |
| *G06K 9/62* | (2006.01) |

(52) U.S. Cl.
CPC ......... *G06K 9/4604* (2013.01); *G06K 9/4661* (2013.01); *G06K 9/6205* (2013.01); *G06T 7/0008* (2013.01); *G06T 7/11* (2017.01); *G06T 7/12* (2017.01); *G06T 7/13* (2017.01); *G06T 7/60* (2013.01); *G06T 2207/30108* (2013.01); *G06T 2207/30164* (2013.01)

(56) References Cited

U.S. PATENT DOCUMENTS

| | | | | |
|---|---|---|---|---|
| 2013/0022280 | A1* | 1/2013 | Liu .................. | G06K 9/4671 |
| | | | | 382/224 |
| 2013/0315486 | A1* | 11/2013 | Franz ................ | G01N 21/9027 |
| | | | | 382/190 |
| 2014/0112558 | A1* | 4/2014 | Bean ................. | G06K 9/46 |
| | | | | 382/128 |
| 2014/0141465 | A1* | 5/2014 | Furrer .............. | G01N 35/00732 |
| | | | | 435/29 |
| 2014/0153834 | A1* | 6/2014 | Poyil ................ | G06K 9/00818 |
| | | | | 382/199 |
| 2016/0025757 | A1* | 1/2016 | Pollack ............. | G01N 21/253 |
| | | | | 348/143 |
| 2018/0047150 | A1* | 2/2018 | Chang ................ | G06T 7/0008 |

OTHER PUBLICATIONS

Xing Chen et al: "A new concentric circle detection method based on Hough transform", Computer Science&Education (ICCSE), 2012 7TH International Conference on, IEEE, Jul. 14, 2012 (Jul. 14, 2012), pp. 753-758, XP032232692, DOI: 10.1109/ICCSE_2012. 6295182 ISBN:978-1-4673-0241-8 *abstract* *p. 754, col. 1, paragraph 2*.

Lagger P et al: "Retrieving multiple light sources in the presence of specular reflections and texture", Computer Vision and Image Understanding, Academic Press, US, vol. 111, No. 2, Aug. 1, 2008 (Aug. 1, 2008), pp. 207-218, XP022932215, ISSN: 1077-3142, DOI: 10.1016/J.CVIU.2007.11.002 [retrieved on Dec. 3, 2007] *abstract*.

Extended EP Search Report dated Jan. 24, 2018 of corresponding European Application No. 167529205, 5 Pages.

PCT International Search Report and Written Opinion dated May 5, 2016 (14 Pages).

Lacey. "Histograms of Orientation Gradients," School of Computer Science & Statistics Trinity College Dublin, 2011, [retrieved on Apr. 1, 2016]. Retrieved from the internet: <URL:https://www.scss.tcd. le/Gerard.Lacey/Gerard_Lacey_Homepage/CS4053_Course_files/Lecture%20009%20HOG-HOF.pdf>. pp. 1-29.

* cited by examiner

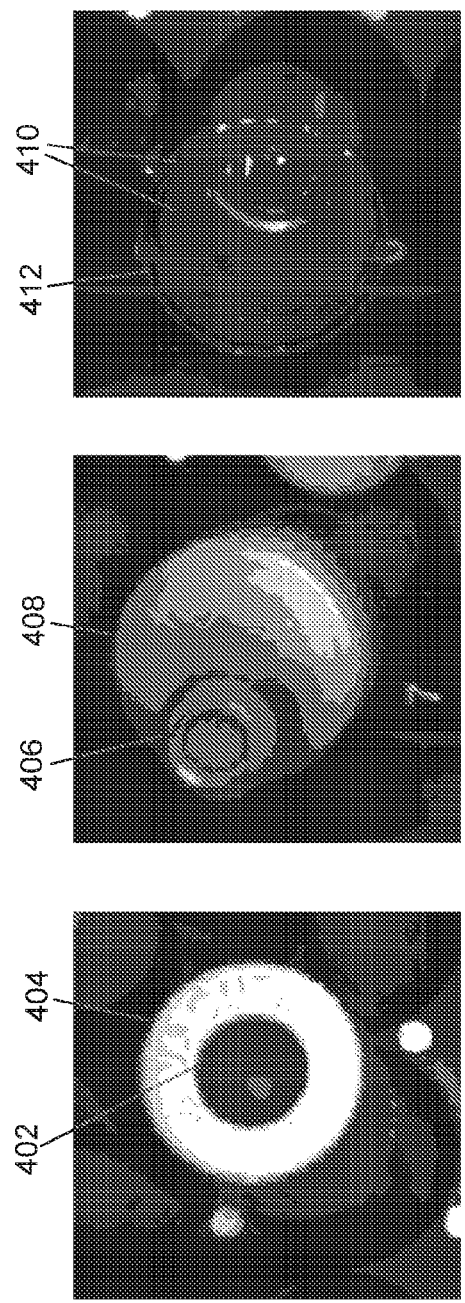
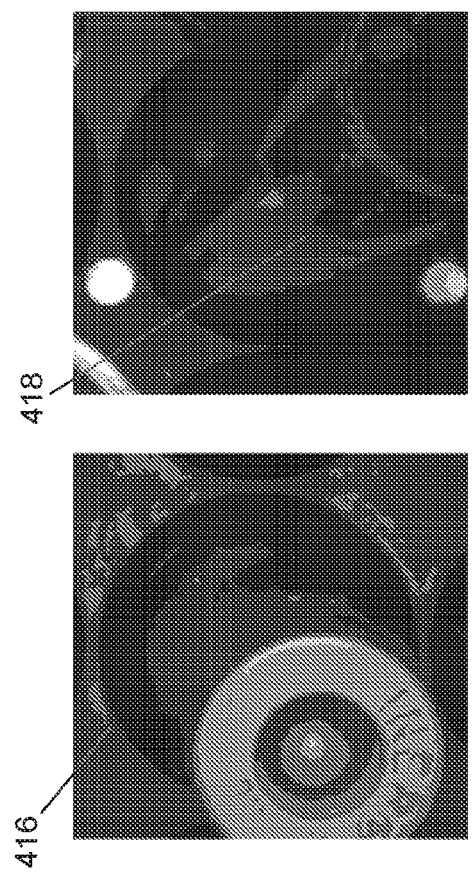
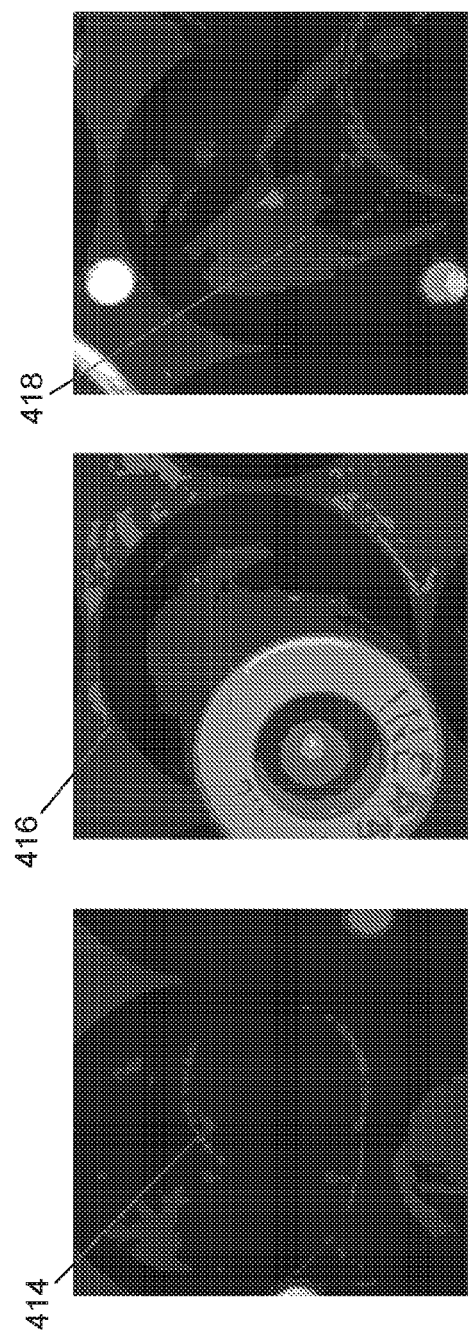
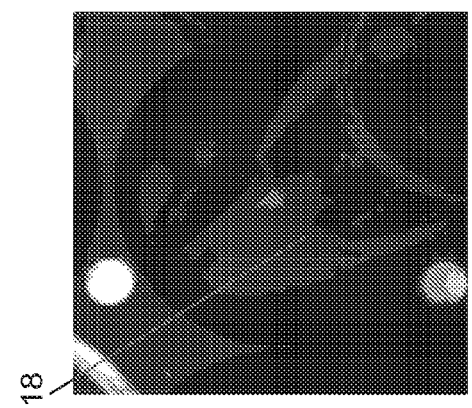
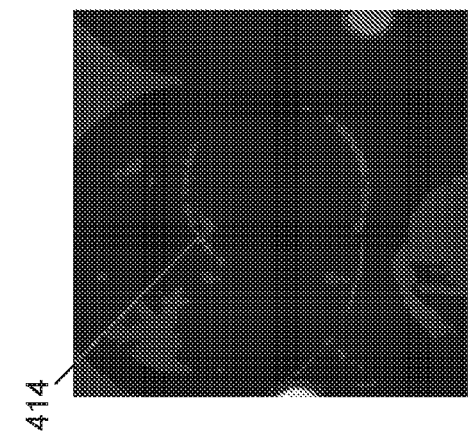
FIG. 4A  FIG. 4B  FIG. 4C  FIG. 4D  FIG. 4E  FIG. 4F

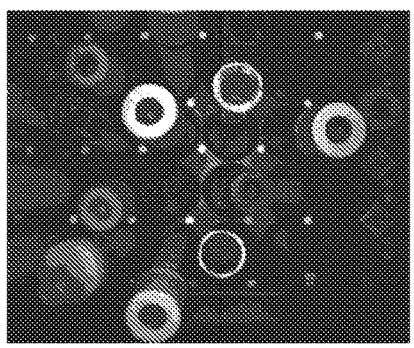
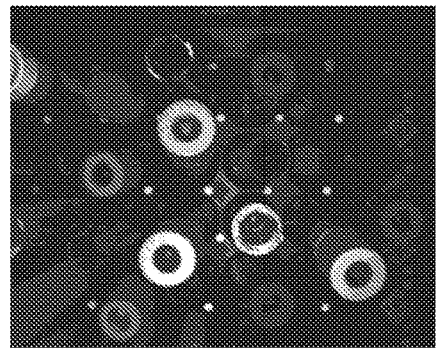
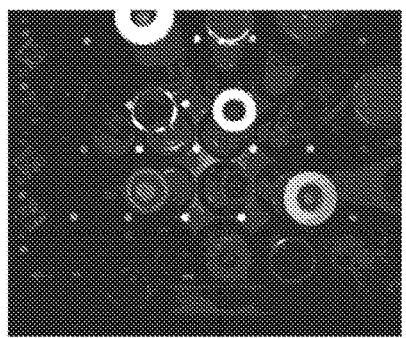
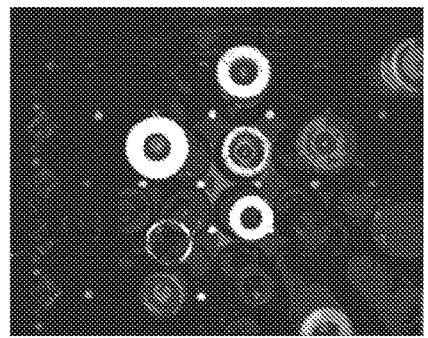

IMAGE-BASED TUBE SLOT CIRCLE DETECTION FOR A VISION SYSTEM

RELATED APPLICATION

This application claims priority to U.S. Provisional Application Ser. No. 62/117,914 entitled "IMAGE-BASED TUBE SLOT CIRCLE DETECTION FOR A VISION SYSTEM" filed on Feb. 18, 2015, the disclosure of which is hereby incorporated by reference in its entirety herein.

TECHNOLOGY FIELD

The embodiments disclosed herein relate in general to capturing images of a tube tray to determine characteristics of the tubes held within the tray and, more particularly, to using image-based tube top circle detection for accurate determination of the characteristics of the tubes held within the tray.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) into which tubes or vials containing patient samples have been loaded. Because of the variety of assays needed in a modem IVD lab, and the volume of testing necessary to operate a lab, multiple analyzers are often employed in a single lab. Between and amongst analyzers, automation systems may also be used. Samples may be transported from a doctor's office to a lab, stored in the lab, placed into an automation system or analyzer, and stored for subsequent testing.

Storage and transport between analyzers is typically done using trays. A tray is typically an array of several patient samples stored in test tubes. These trays are often stackable and facilitate easy carrying of multiple samples from one part of the laboratory to another. For example, a laboratory may receive a tray of patient samples for testing from a hospital or clinic. That tray of patient samples can be stored in refrigerators in the laboratory. Trays of patient samples can also be stored in drawers. In some automation systems, an analyzer can accept a tray of patient samples and handle the samples accordingly, while some analyzers may require that samples be removed from trays by the operator and placed into carriers (such as pucks) before further handling. Trays are generally passive devices that allow samples to be carried and, in some cases, arranged in an ordered relationship.

Generally, information about sample tubes stored in a tray is not known until an operator or sample handling mechanism interacts with each tube. For example, a sample handling robot arm may pick up a tube, remove it from the tray, and place it into a carrier. The carrier can then travel to a decapper station to remove any possible cap and pass by a barcode reader so that a barcode on the side of the tube can be read to reveal the contents of the tube. In many prior art sample handling mechanisms, the identity of the tube is not known until after the tube is removed from the tray. In this manner, all tubes in a tray will often be handled the same way until after a tube is placed onto a carrier in an automation system.

SUMMARY

Embodiments provide a method of using image-based tube top circle detection. The method includes receiving, from at least one camera, a series of images of a tray. The tray includes a plurality of tube slots. Each tube slot is configured to receive a sample tube. The series of images of the tray are acquired via the at least one camera. The method also includes extracting, using a processor, a region of interest (ROI) patch from one of the series of images. The ROI patch includes a target tube top circle and has boundaries constrained by two dimensional (2D) projections of a plurality of different types of tube top circle centers according to heights and diameters of a plurality different types of sample tubes. The method also includes calculating, using the processor, an edge gradient magnitude map of the extracted ROI patch and constructing, using the processor, a three dimensional (3D) map of a circle parameter space, where each location in the 3D map corresponds to a circle parameter having a center location and a diameter. The method also includes accumulating, using the processor, weighted votes in the 3D map from edge points in the edge gradient magnitude map along gradient directions of each of the edge points and determining, using the processor, one or more locations in the 3D map as a circle candidate when the accumulated votes in the 3D map are equal to or greater than a predetermined threshold. The method further includes selecting, using the processor, the determined circle candidate having the greatest accumulated votes as the target tube top circle.

According to an embodiment, the tray is configured to fit within a portion of a drawer movable between an open position and a closed position and the image of the tray is acquired via the at least one camera as the drawer is moved between the open and the closed position.

According to another embodiment, the method further includes predicting, using the processor, the two dimensional (2D) projection of each of the plurality of different types of tube top circle centers based on an intrinsic calibration of the at least one camera and an extrinsic pose with respect to a surface of the tray. The method further includes constraining, using the processor, the boundaries of the ROI patch based on maximum and minimum settings of the plurality of different types of sample tubes, the maximum and minimum settings comprising: (i) a highest tube with a largest diameter; (ii) the highest tube with a smallest diameter; (iii) a shortest tube with the largest diameter; and (iv) the shortest tube with the smallest diameter.

According to yet another embodiment, the method further includes determining, using the processor, a polygon that defines an area which the target tube top circle center is located based on the maximum and minimum settings.

In one embodiment, selecting the determined circle candidate having the greatest accumulated votes as the target tube top circle further includes determining (i) whether the center of the circle is equal to or less than a predetermined distance threshold of a center of another circle candidate; and (ii) whether an area of the circle candidate and an area of the other circle candidate have an overlap equal to or greater than a predetermined overlap threshold. When both (i) and (ii) are determined to be true, the circle candidate or the other circle candidate having the smaller diameter is eliminated from being a circle candidate. If the diameters are equal, the circle candidate or the other circle candidate having the smaller amount of accumulated votes is eliminated from being a circle candidate. When either (i) or (ii)

is determined to be false, the circle candidate is ranked with other circle candidates according to the amount of accumulated votes.

In another embodiment, accumulating the weighted votes in the 3D map from the edge points in the edge gradient magnitude map along the gradient directions of each edge points further includes determining a line intersecting each edge point along the gradient directions of each edge point and assigning one or more of the weighted votes to points on the line that are equal to or within a predefined distance from each edge point.

In an aspect of an embodiment, accumulating the weighted votes in the 3D map from the edge points in the edge gradient magnitude map along the gradient directions of each edge points further includes assigning greater weight to votes for points along positive gradient directions of each edge point than votes for points along negative gradient directions of each edge point.

According to an embodiment, the method further includes determining, using the processor, specular points in the ROI patch and assigning, using the processor, a first weight to votes along positive gradient directions of each specular point and assigning a second weight to votes along negative gradient directions of each specular point, wherein the first weight and the second weight are equal. The method further includes accumulating, using the processor, the votes in the 3D map from the specular points along the positive gradient directions of each specular point and the negative gradient directions of each specular point.

According to another embodiment, the method further includes constructing, using the processor, a 2D map of the circle center parameter space, each location of the 2D map corresponding to a circle center location and determining, using the processor, accumulated weighted votes for the 2D map from edge points in the edge gradient magnitude map along the gradient directions of each edge point and filtering out, using the processor, one or more rows in the 3D map when the accumulated votes at corresponding locations on the 2D map are lower than a predefined threshold.

In yet another embodiment, the method further includes constructing, using the processor, a 2D map of the circle center parameter space, each location of the 2D map corresponding to a specific center location, determining, using the processor, accumulated weighted votes for the 2D map from edge points in the edge gradient magnitude map along the gradient directions of each edge point and ranking, using the processor, the 2D circle center locations in the 2D map according to accumulated weighted votes in the 2D map.

Embodiments provide a vision system for use in an in vitro diagnostics environment. The system includes a tray having a plurality of tube slots arranged in a matrix of rows and columns. Each tube slot configured to receive a sample tube. The system also includes a surface configured to receive the tray and at least one camera configured to capture a series of images of the tray as the drawer is moved. The system further includes a processor configured to extract a region of interest (ROI) patch from one of the series of images, the ROI patch including a target tube top circle and having boundaries constrained by two dimensional (2D) projections of a plurality of different types of tube top circle centers according to heights and diameters of a plurality different types of sample tubes. The processor is also configured to calculate an edge gradient magnitude map of the extracted ROI patch and construct a three dimensional (3D) map of a circle parameter space where each location in the 3D map corresponds to a circle parameter having a center location and a diameter. The processor is also configured to accumulate weighted votes in the 3D map from edge points in the edge gradient magnitude map along gradient directions of each of the edge points and determine one or more locations in the 3D map as a circle candidate when accumulated votes at the one or more locations in the 3D map is equal to or greater than a predetermined threshold. The processor is further configured to select the determined circle candidate having the greatest accumulated votes as the target tube top circle.

Embodiments provide a method of using image-based tube top circle detection. The method includes receiving, from at least one camera, a series of images of a tray comprising a plurality of tube slots, each tube slot configured to receive a sample tube, the series of images of the tray being acquired via the at least one camera. The method also includes extracting, using a processor, a region of interest (ROI) patch from one of the series of images, the ROI patch comprising a target tube top circle and having boundaries constrained by two dimensional (2D) projections of a plurality of different types of tube top circle centers according to heights and diameters of a plurality different types of sample tubes. The method also includes calculating, using the processor, an edge gradient magnitude map of the extracted ROI patch and constructing, using the processor, a 2D map and a three dimensional (3D) map of a circle parameter space, each location in the 2D map corresponding to a circle center location and each location in the 3D map corresponding to a circle center and a diameter parameter. The method also includes accumulating, using the processor, weighted votes in the 2D map and in the 3D map based on edge points in the edge gradient magnitude map along gradient directions of each edge point and determining, using the processor, one or more locations in the 2D map having accumulated votes larger than a first predetermined threshold. The method further includes determining, using the processor, the corresponding locations in the 3D map as circle candidates when accumulated votes at the corresponding locations in the 3D map are equal to or greater than a second predetermined threshold and selecting, using the processor, the determined circle candidate having the greatest accumulated votes as the target tube top circle.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following Figures:

FIG. 4A through FIG. 4F are exemplary images of sample tubes having different sample tube appearances according to embodiments described herein;

FIG. 10A through FIG. 10D show sample images of a tube offset tool used to evaluate the performance of tube top circle detection according to embodiments disclosed herein;

DESCRIPTION OF EXEMPLARY EMBODIMENTS

Figure 1A:
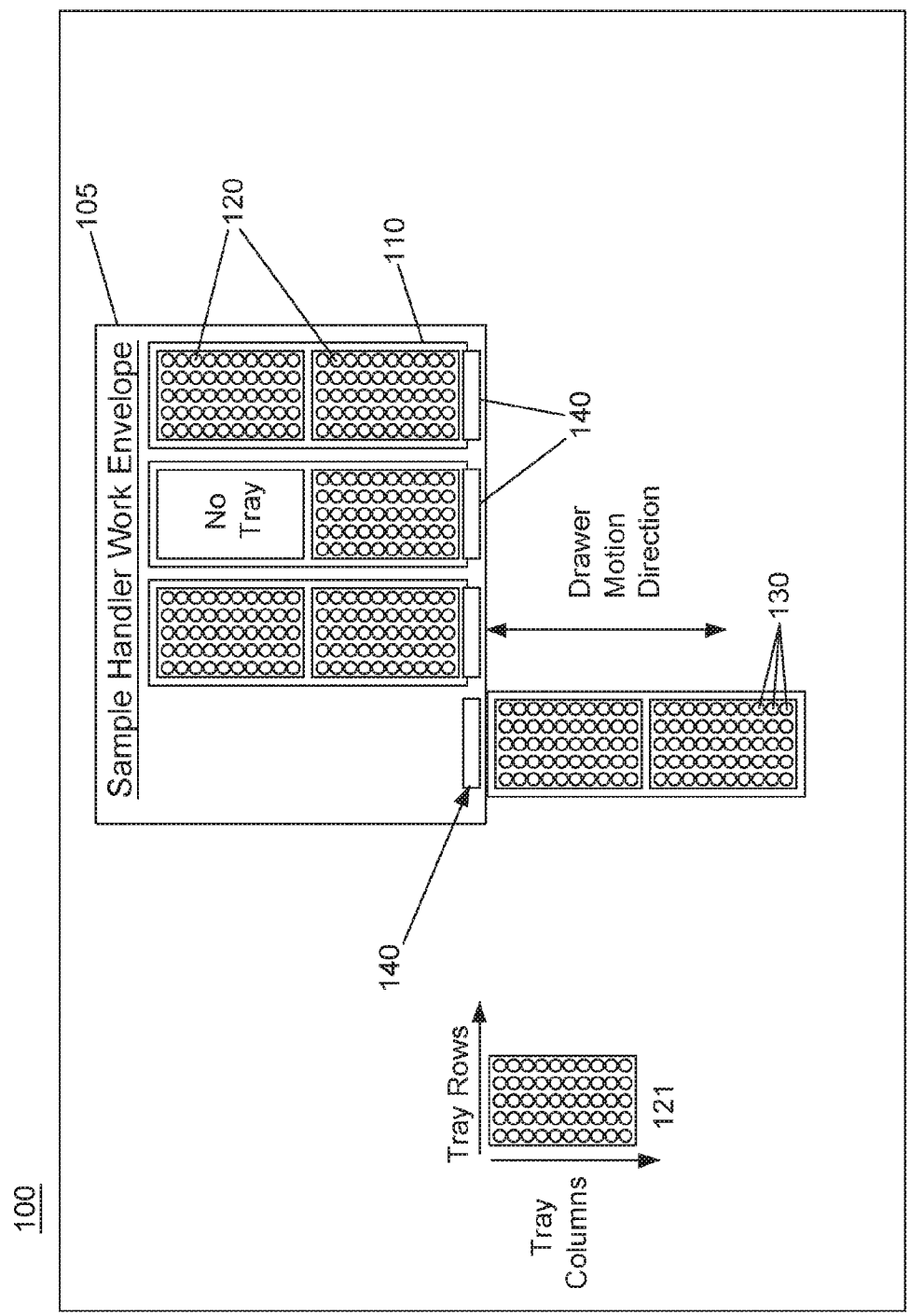
FIG. 1A is a representation of a system for characterizing through image analysis tube trays and tubes held in a drawer, according to an embodiment.

This application relates to several of the concepts described in PCT Application No.: PCT/US14/27217, and U.S. Patent Application No. 62/010,370 to Wu et al., which are incorporated, herein by reference.

Embodiments include systems and methods for determining categories and characteristics of tubes held within a tube tray in an automated vision system configured to acquire images of the tube trays and tubes held within the tube trays. Some embodiments include acquiring images of trays that are manually placed and aligned in an automation system. For example, automation systems may provide a flat surface with guide rails and allow the operator to manually align keying features on the trays to the rails and push the trays to the working area.

Some embodiments may include an automated drawer vision system (DVS) comprising a drawer for loading and unloading tube trays on which sample tubes are contained. The images of the trays may be acquired via one or more cameras, mounted above an entrance area of the drawer, as the drawer is moved between an open position and a closed position (e.g., working area position).

Embodiments analyzed the acquired images to determine the tube categories and tube characteristics. Embodiments use image-based tube top circle detection to localize the tube top circle region in the input images. The tube top circle region may be utilized to determine the categories and characteristics of tubes having variation in their appearances. For example, the two dimensional (2D) projections in an image may be predicted for each possible tube top circle and/or tube top circle center. Region of interest (ROI) patches may be extracted from the image using physical sample tube geometry constraints. Constraints may include maximum and minimum 2D projections of tube heights and tube diameters. Embodiments also use edge gradient magnitude for edge strengths and extract specular points of tubes in an image to capture the trace of a tube top circle.

For a ROI having multiple circles within a camera's view, embodiments determine categories or characteristics of a tube using a three dimensional (3D) mapping algorithm, such as a 3D Hough transform to determine a circle's center and radius (or diameter) simultaneously. An optimal circle may be selected from one or more circle candidates based on criteria derived from sample tube geometry and appearances.

As described in PCT Application No.: PCT/US14/27217, a tube tray of a DVS is configured to fit within a drawer and hold a plurality of tubes in slots that are arranged in an array of rows and columns. The images are used to characterize the tray as well as the tubes held on the tray. In particular, according to embodiments, by analyzing the images, various features of the tubes can be determined, such as, for example, the tray slots containing a tube; a tube's center point in a coordinate system, a tube's diameter and height; the tray's orientation within a drawer; whether a tube is a plain tube, the tube is covered with a cap or tube-top sample cup; a tube cap's color(s), a barcode on a tray surface; and a speed at which a drawer holding the tray is being inserted or removed into the work environment. Embodiments determine this information and other pieces of information quickly, without expensive equipment, and without handling or touching the tubes. Such knowledge allows for an efficient and streamlined processing of the tubes, as well as for reduced setup and maintenance costs.

This information is valuable in an IVD environment in which a sample handler is processing the tubes and moving the tubes to analyzers for testing and analysis. Embodiments of the present invention are particularly well suited for, but in no way limited to, IVD environments.

FIG. 1A is a representation of an exemplary drawer vision system 100 in which tube trays 120 and tubes 130 contained thereon are characterized by obtaining and analyzing images thereof, according to an embodiment. One or more drawers 110 are movable between an open and a closed position and are provided in a work envelope 105 for a sample handler. One or more tube trays 120 may be loaded into a drawer 110 or may be a permanent feature of the drawer 110. Each tube tray 120 has an array of rows and columns of slots (as depicted in exemplary tray 121) in which tubes 130 may be held.

According to embodiments, images are taken of a tube tray 120. The images are analyzed to determine characteristics of the tube tray 120 and the tubes 130. A moving-tray/fixed camera approach is used, according to embodiments provided herein, to capture the images for analysis thereof. As the tube tray 120 is moved into the work envelope 105 by, for example, manually or automatically pushing in the drawer 110, an image capture system 140 is used to take images of the tube tray 120 and the tubes 130 contained thereon.

The image capture system 140 may include one or more cameras (e.g., left camera 242 and right camera 244 shown in FIG. 2) positioned at or near the entrance to the work envelope 105. In some embodiments, the one or more cameras 242, 244 may be positioned above the surface of the tube tray 120. For example, the cameras 242, 244 may be placed three to six inches above the surface to capture a high resolution image of the tube tray 120. Other distances and/or positioning may also be used depending on the features of the cameras 242, 244 and the desired perspective and image quality. Optionally, the image capture system 140 may include one or more lighting sources, such as an LED flash.

Figure 1B:
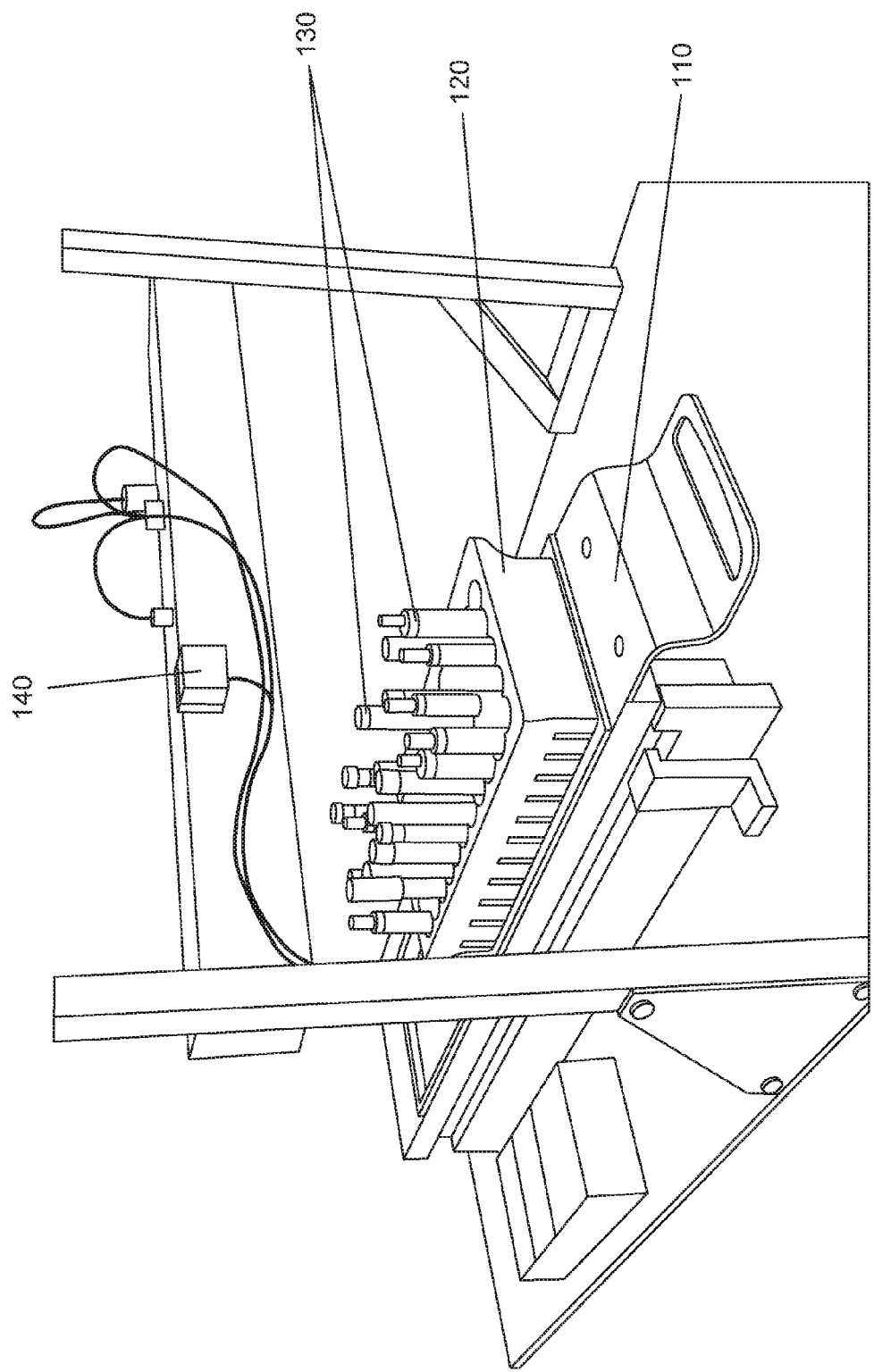
FIG. 1B shows an exemplary drawer vision system test harness including an image capture system positioned above a tube tray disposed on a drawer, according to an embodiment.

FIG. 1B shows an exemplary test harness of an exemplary drawer vision system that may be used with embodiments disclosed herein. As shown in FIG. 1B, image capture system 140 is positioned above the surface of the tube tray 120 holding tubes 130 and disposed on drawer 110. The drawer 110 shown in the embodiment at FIG. 1B is configured to hold two 55-slot trays or six 15-slot trays. Embodiments may, however, include trays configured to hold trays having different numbers of slots and having different sizes.

Figure 2:
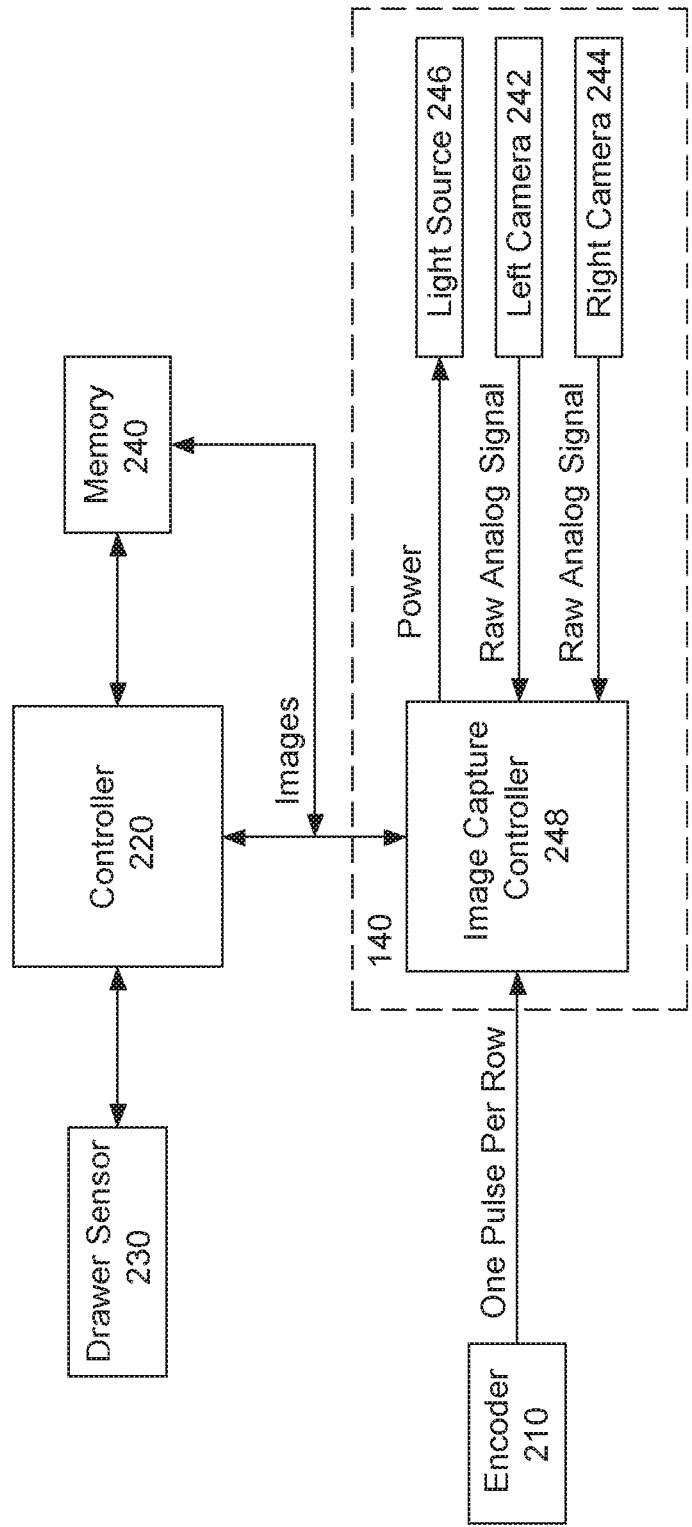
FIG. 2 shows a block diagram representation of a system for characterizing, through image analysis, the tube trays and the tubes contained thereon held in a drawer, according to an embodiment.

FIG. 2 shows a block diagram representation of an exemplary system 200 for characterizing, through image analysis, the tube trays 120 and the tubes 130 contained thereon held in a drawer 110, according to an embodiment. The image capture system 140, according to an embodiment, includes two cameras, a left camera 242 and a right camera 244. Additional or fewer cameras may be included depending on the size of the drawers 110 and the tube trays 120, as well as the desired image quality and image perspective. A light source 246 and an image capture controller 248 are also part of the image capture system 140.

An encoder 210, such as a quadrature encoder may be used to determine when a row of the tube tray 120 is moved into a centered or substantially centered position beneath the one or more cameras 242, 244. The encoder 210 transmits a signal (i.e., a pulse) to the image capture controller 248 upon detection of movement of the tube tray 120 corresponding to a new row of the tube tray 120 moving into a centered or substantially centered position beneath the one or more cameras 242, 244. The signal serves as an instruction for the image capture controller 248 to instruct the cameras 242, 244 to take an image upon receipt of the signal.

A controller 220 is provided for managing the image analysis of the images taken by the cameras 242, 244. Upon detection of the closing of the drawer 110, the image capture controller 248 provides the images to the controller 220 for downloading and processing. The controller 220 is, according to an embodiment, part of a sample handler that is used in the IVD environment to handle and move the tube trays 120 and the tubes 130 between storage locations, such as the work envelope 105, to analyzers. The image analysis performed by the controller 220 serves to instruct the sample handler on the various determined characteristics of the tube tray 120 and the tubes 130, thus allowing the sample handler to accordingly handle and process the tube tray 120 and the tubes 130.

The one or more memory devices 240 are associated with the controller 220. The one or more memory devices 240 may be internal or external to the controller 220.

One or more drawer sensors 230 may be connected to the controller 220 to indicate when the drawer 110 is fully closed and/or when the drawer 110 is fully opened. According to an embodiment, the drawer 110 being fully closed serves as an indication to begin image processing of the captured and stored images. When the drawer 110 is fully closed, the drawer sensor 230 sends a signal to the controller 220.

Figure 3:
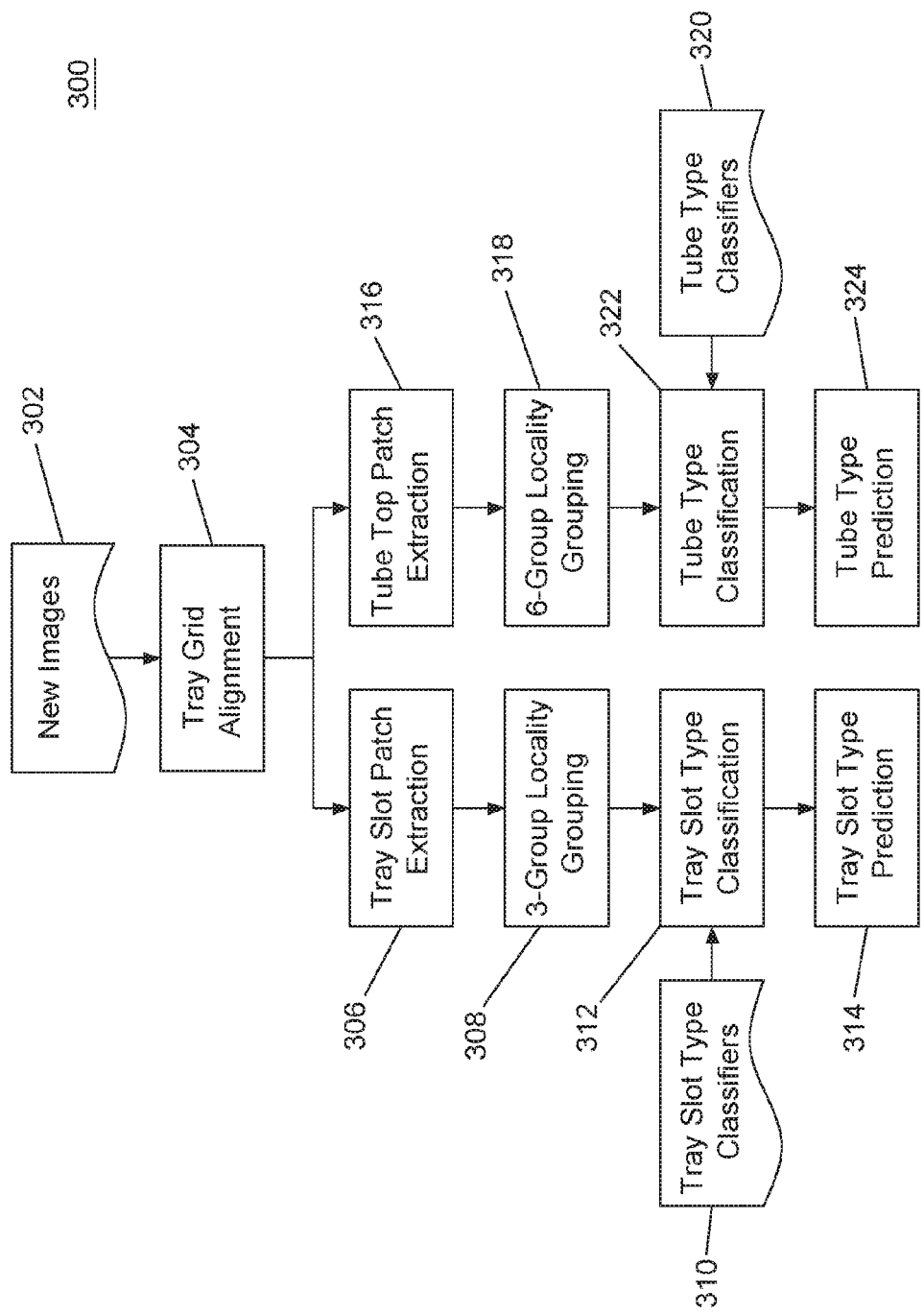
FIG. 3 is a flowchart illustrating a method of detecting properties of sample tubes according to embodiments described herein.
Figure 5C:
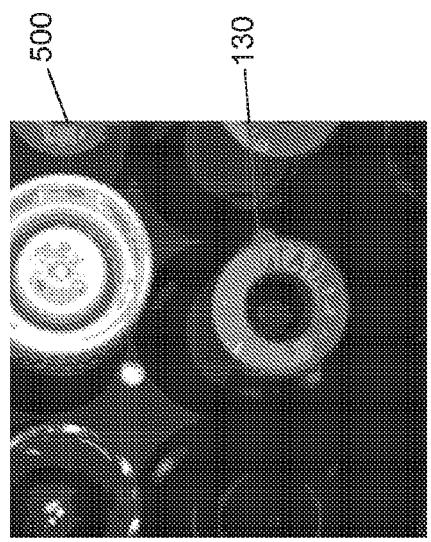
FIG. 5A, FIG. 5C, FIG. 5E and FIG. 5G are exemplary images showing views from a camera of portions of a tray having different tubes of interest according to embodiments described herein.
Figure 5D:
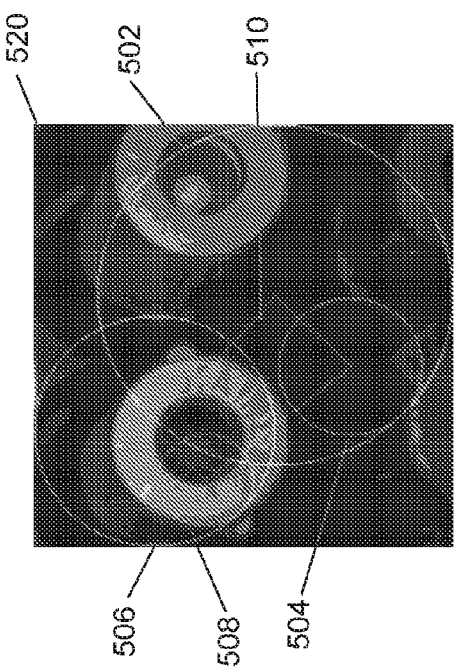
FIG. 5B, FIG. 5D, FIG. 5F and FIG. 5H are exemplary extracted ROI image patches that constrain the search areas shown in the images 500 at FIG. 5A, FIG. 5C, FIG. 5E and FIG. 5G, respectively according to embodiments described herein.
Figure 5A:
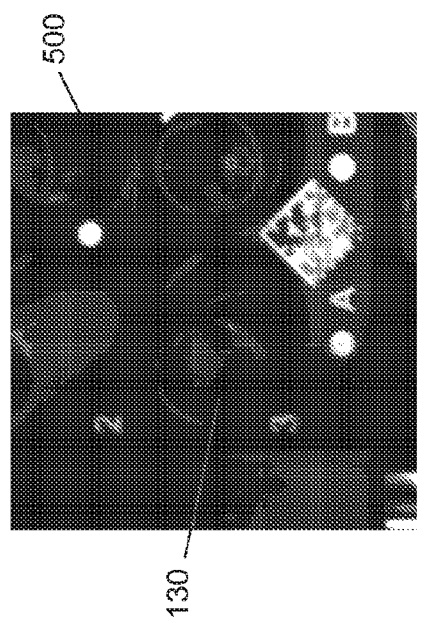
Figure 5B:
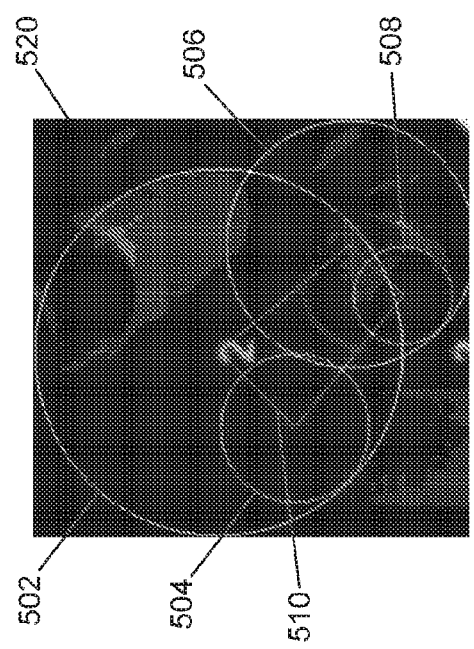
Figure 5G:
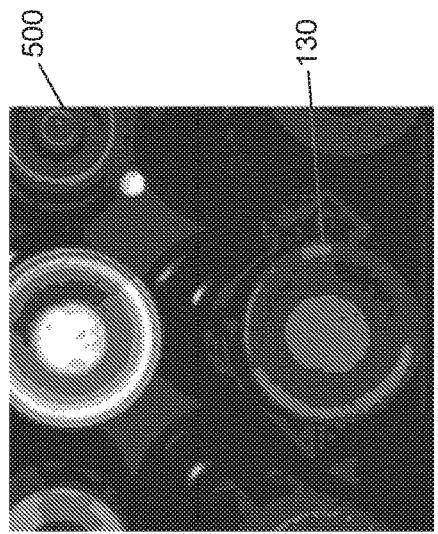
Figure 5H:
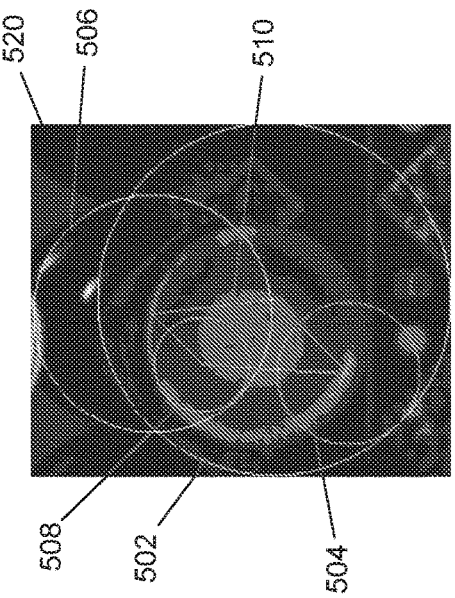
Figure 5E:
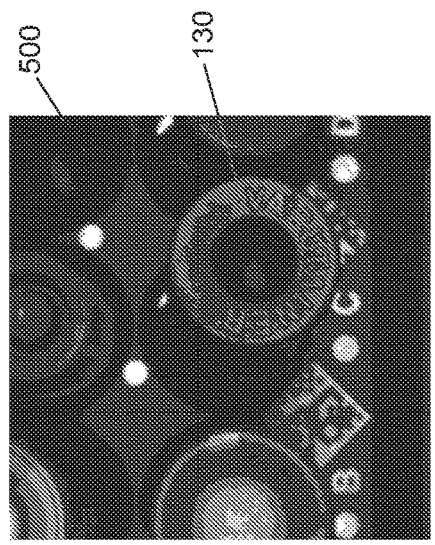
Figure 5F:
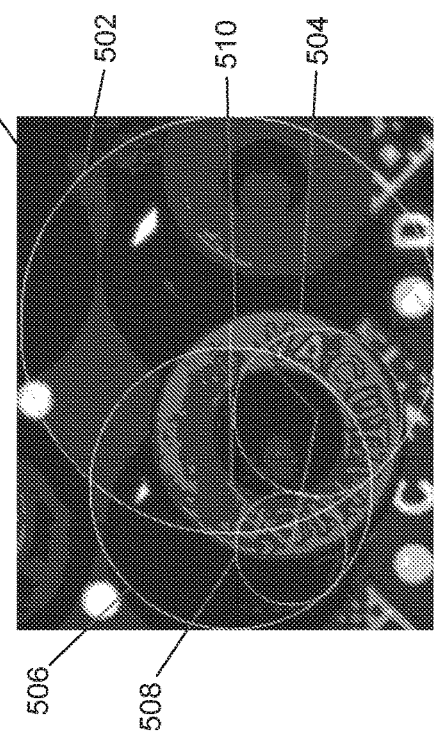

FIG. 3 is a flowchart illustrating an exemplary method 300 of determining tray slot types and tube types of sample tubes within which embodiments of the present disclosure may be implemented. As shown in FIG. 3, the exemplary method may determine a tray slot type (e.g., whether slot is empty or not empty) via steps 306-314 and/or may determine a tube type (e.g., plain tube, tube with a cap or tube with a tube-top sample cup) via steps 316-324. Exemplary methods of determining a tray slot type and a tube type are described in application 62/117,916 entitled "Locality-Based Detection of Tray Slot Types and Tube Types in a Drawer Vision System," which is incorporated herein by reference and is being filed concurrently with the present application.

Embodiments described herein using image-based tube-top circle detection may be implemented as part of the method 300. For example, after the images are acquired at step 302 and the tray grid is aligned at step 304, embodiments described herein using image-based tube top circle detection may be used to extract tube top patches at step 316 of FIG. 3 prior to proceeding to steps 318-324 to determine a tube type. Embodiments may, however, be used as part of other methods to determine tube types. The following description is directed to embodiments using image-based tube top circle detection.

Conventional automation systems lack advanced tube categorization and characterization capabilities. The exemplary drawer vision system 100 utilizes cameras 242, 244 mounted on top of the drawer entrance to acquire images of the sample tubes 130 during drawer insertion. The acquired images may then be analyzed to determine tube categorization and tube characterization.

A camera's view of a sample tube 130 may be partially occluded by other sample tubes 130 in a tray 120 or self-occluded due to perspectives. Because a top circle of a tube 130 is less likely to be occluded than other portions of a tube 130, embodiments determine a category and/or a characteristic of a tube 130 based on the top circle of a tube 130.

FIG. 4A through FIG. 4F are exemplary images of sample tubes 130 having different sample tube appearances. A 2D projection of the tube top circle may be estimated because of the proximity of the sample tube 130 to the cameras 242, 244 when an image of the sample tubes 130 is acquired. Conventional circle detection algorithms such as Hough transform based approaches may be used for circle detection. Variation of the sample tube appearances, however, poses challenges to accurate circle detection using conventional circle detection algorithms.

For example, some tube tops may include circles within circles. As shown in FIG. 4A, a capped tube may include an inner circle 402 in the middle of the outer circle 404 of the cap. As shown in FIG. 4B, a hat on top of the cap base may form an inner circle 406 within an outer circle 408 of the base in its 2D projection. As shown in FIG. 4C, a tube top sample cup may include a circular sample cup on top of a plain tube, where multiple circles 410 may be observed from the ring of the sample cup as well as the underlying plain tube top circle 412. Conventional circle detection algorithms, such as 2D Hough transform based approaches cannot accurately detect circles within circles as these algorithms try to seek the circle center first and then decide the best diameter. Circles within circles may interfere with the circle center search and the best diameter in terms of either size or edge counts may not be optimal for tube circle detection.

Edge strengths of different types of sample tubes, sample cups and caps may vary. Binary edge maps used in conventional circle detection algorithms are not sufficient for accurately detecting circles of sample tubes, sample cups and caps having mixed edge strengths. Binary edge maps may contain either too few responses to capture weak edges or too many responses that interfere with the circle center and diameter search. In some cases, irregular reflection on the tube top circle exhibits sparse specular spots 414 instead of connected edges, as shown in FIG. 4D, which breaks conventional circle detection algorithms that purely rely on edge detection as the preprocessing step.

Portions of tube slots circles 416 (as shown in FIG. 4E) and portions of tube label boundaries 418 (as shown in FIG. 4F), both of which are not tube top circles, may include circular patterns having strong edges which may interfere the circle detection if not properly filtered out by the physical sample tube geometry constraints. Sample tubes from nearby slots may also interfere with the circle detection if not properly filtered out by the physical sample tube geometry constraints.

An exhaustive search to determine a tube top circle is time consuming and error-prone. Because a sample tube is held within a tube slot and a sample tube's height and diameter are within a certain range, embodiments described herein efficiently and accurately determine a location of a tube top circle.

FIG. 5A, FIG. 5C, FIG. 5E and FIG. 5G are exemplary images 500 showing views from a camera 242, 244 of portions of a tray 120 having different tubes 130 of interest. FIG. 5B, FIG. 5D, FIG. 5F and FIG. 5H show exemplary extracted ROI image patches 520 having boundaries constrained by tube top circles 502, 504, 506 and 508 according to maximum and minimum diameters and heights of 2D projections of different types of sample tubes 130. The images 500 at FIG. 5A, FIG. 5C, FIG. 5E and FIG. 5G illustrate fixed distance areas with respect to the tubes 130 of interest. These areas in images 500 may, however, be constrained to a region of interest (ROI) for more accurate tube top circle detection. For example, using information determined from the camera's intrinsic calibration and extrinsic pose with respect to the tray surface, the 2D projection of a tube top circle center may be predicted from its tube slot location, tube height, and tube diameter. An area of a tray 120 may be constrained to the ROI based on the location of possible 2D projections of a tube top circle and a tube top circle center. A ROI patch may then be extracted, using a processor such as controller 220, from one of the images 500.

The extracted ROI image patches 520 shown in FIG. 5B, FIG. 5D, FIG. 5F and FIG. 5H constrain the search areas in the images 500 shown in FIG. 5A, FIG. 5C, FIG. 5E and FIG. 5G, respectively. As shown in the embodiments illustrated in FIG. 5B, FIG. 5D, FIG. 5F and FIG. 5H, the maximum and minimum settings may include: (i) the highest tube with the largest diameter, as indicated by circles 502; (ii) the highest tube with the smallest diameter, as indicated by circles 504; (iii) the shortest tube with the largest diameter, as indicated by circles 506; and (iv) the shortest tube with the smallest diameter, as indicated by circles 508. Based on the maximum and minimum settings a polygon 510 may then be determined which defines an area in which a tube top circle center may be located. As shown, the corners of the polygon 510 correspond to the tube top circle centers of the circles 502, 504, 506 and 508. Based on the maximum and minimum settings 502, 504, 506 and 508 and the polygon 510, a ROI may be determined, using a processor such as controller 220, that is constrained to boundaries where the 2D projections of the possible tube top circles may be observed, providing a better search area for tube top circle detection. The extracted ROI image patches 520 also follow the perspectives (from the camera's point of view) where a tube 130 may extend from the tray surface to its maximal height. Therefore, tubes 130 from other slots are less likely to be included in the extracted image patches 520.

Figure 6B:
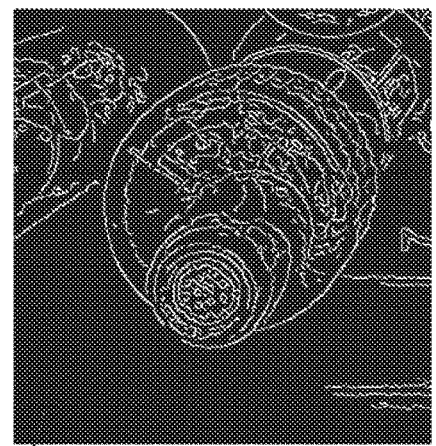
FIG. 6B is a binary edge map of the exemplary image shown in FIG. 6A.
Figure 6C:
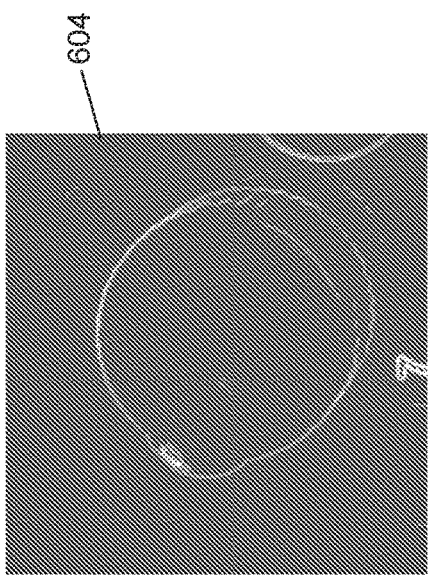
FIG. 6C is an edge gradient magnitude map of the exemplary image shown in FIG. 6A.
Figure 6A:
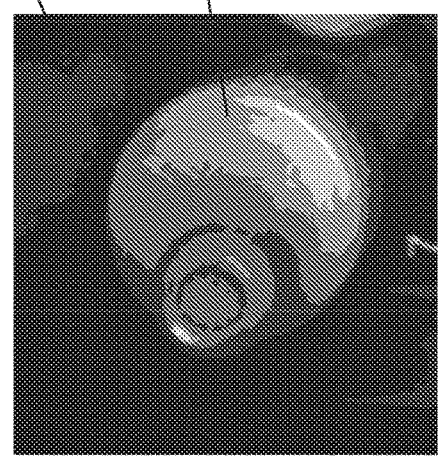
FIG. 6A is an exemplary image from a camera of a tube within the camera's field that may be used according to embodiments described herein.

FIG. 6A is an exemplary image 600 from a camera 242, 244 of a tube 130 within the camera's field of view. FIG. 6B shows a binary edge map 602 of the exemplary image 600 shown in FIG. 6A. FIG. 6C shows an edge gradient magnitude map 604 of the exemplary image shown in FIG. 6A. Because mixed edge strengths existing in an image containing various types of sample tubes, conventional binary edge detection methods such as Canny edge detection are not sufficient for accurate circle detection. Embodiments described herein utilize edge gradient magnitude to preserve the original strength of each edge in an image. For example, the edge gradient magnitude map at FIG. 6C preserves the original strength of edges in the original image at FIG. 6A than the binary edge map at FIG. 6B. A processor, such as controller 220, may be used to calculate an edge gradient magnitude map (e.g., map at FIG. 6C) of an extracted ROI patch. According to embodiments described in more detail below, accumulated edge strength may be used to compare multiple circle candidates for optimal circle selection. The edge strengths provided by edge gradient magnitude provides a better measurement for determining optimal circle selection when using the accumulated edge strength to compare multiple circle candidates for optimal circle selection.

Figure 7A:
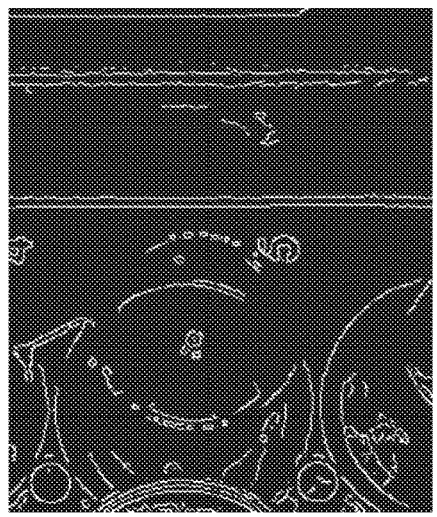
FIG. 7A is an exemplary extracted ROI image patch of a tube within the camera's field of view that may be used according to embodiments described herein.
Figure 7B:
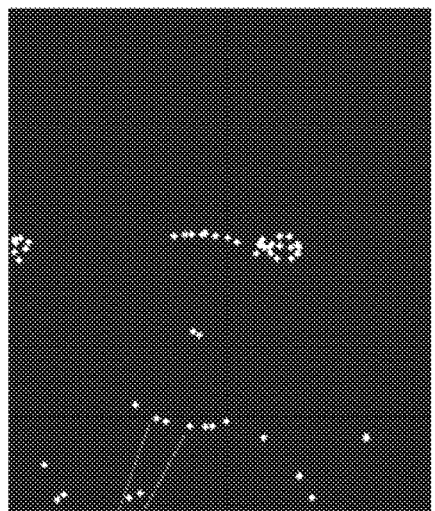
FIG. 7B is a binary edge map of the exemplary extracted ROI image patch shown at FIG. 7A.
Figure 7C:
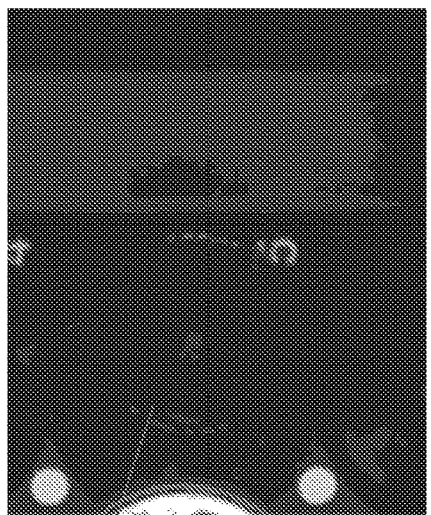
FIG. 7C is an edge gradient magnitude map of the exemplary extracted ROI image patch shown at FIG. 7A.
Figure 7D:
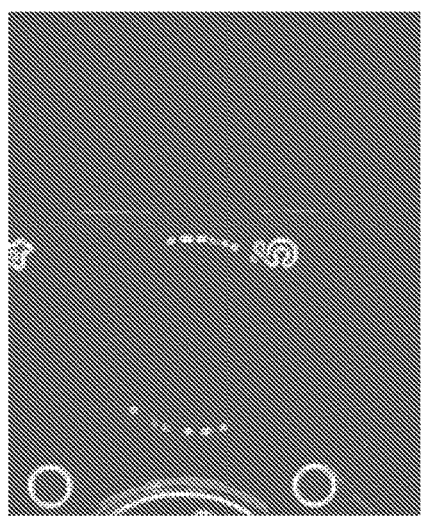
FIG. 7D is a map showing the extracted specular points of the exemplary extracted ROI image patch shown at FIG. 7A.

FIG. 7A is an exemplary extracted ROI image patch of a tube 130 within the camera's field of view. FIG. 7B is a binary edge map of the exemplary extracted ROI image patch shown at FIG. 7A. FIG. 7C is an edge gradient magnitude map of the exemplary extracted ROI image patch shown at FIG. 7A. FIG. 7D shows the extracted specular points.

In some embodiments, specular points of objects in images may also be detected for tube top circle detection. For example, specular points, such as the extracted specular points 702 shown in FIG. 7D, may provide very good cues for tube top circle detection, while edge-based approaches may not be sufficient to extract tube top circles with very weak edge magnitude. The specular points 702 may be detected by using corner feature detectors, such as FAST, to capture the trace of the tube top circle when irregular reflection occurs on the tube top surface.

The specular points 702 may be determined, for example by a processor such as controller 220. The controller 220 may assign equal weight to votes along the positive gradient directions and the negative gradient directions of each specular point 702. That is, a first weight may be assigned to votes along the positive gradient directions and a second weight may be assigned to votes along the negative gradient directions that is equal to the first weight. The votes along the positive gradient directions and the negative gradient directions may be accumulated in the 3D map and the 2D map.

Conventional methods for detecting circles in images are not sufficient for detecting circles within circles. For example, in these conventional methods, Hough transform based approaches are typically applied in two steps. First, a 2D Hough transform is used to search the circle centers by accumulating binary edge counts along its gradient direction. Second, for each circle center candidate, a 1D Hough transform is applied to find the best diameter passing through the highest amount of binary edges without looking into its edge gradient direction. While these conventional methods may efficiently locate circular patterns such as coins and cells in an image, they are not suitable to deal with circles within circles. For example, the edge counts accumulated in conventional methods do not differentiate the strength of the edge, such that noisy edge responses and true tube circle edges get equally counted. The best diameter searches in conventional methods may also not detect the optimal tube top diameter because optimal tube top diameters may not have the highest accumulated edge counts. Further, conventional methods neglect the edge gradient direction resulting in the inclusion of edge points that contribute to other circle candidates, such as when there are multiple circles in an image.

Figure 8:
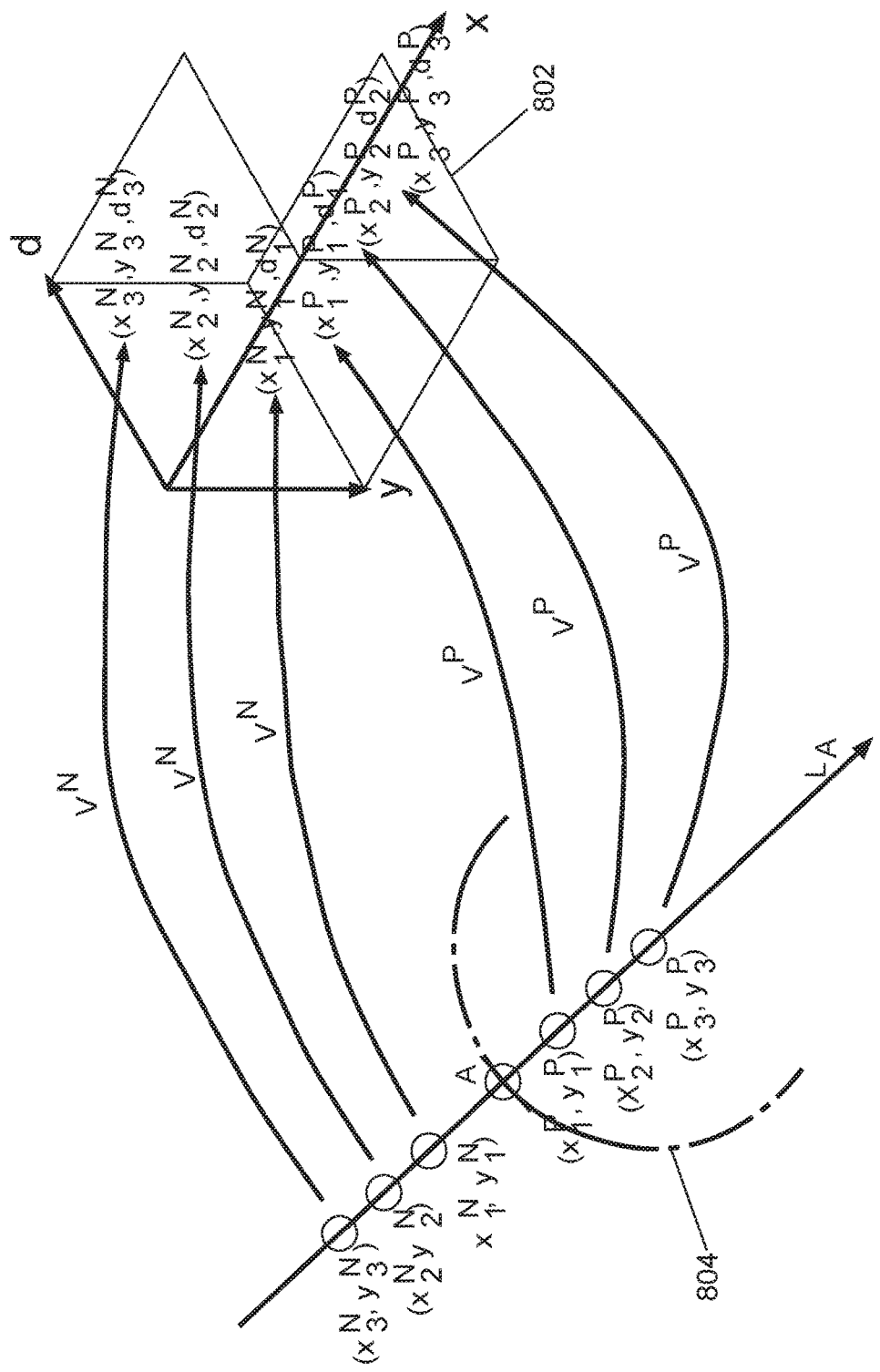
FIG. 8 illustrates part of an exemplary 3D map construction according to embodiments disclosed herein.
Figure 9C:
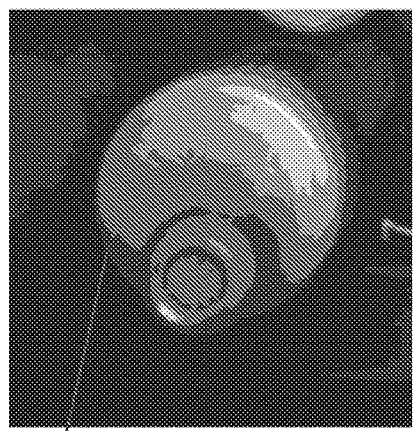
FIG. 9A, FIG. 9C, FIG. 9E and FIG. 9G are exemplary extracted ROI image patches having different target tube top circles according to embodiments disclosed herein.
Figure 9D:
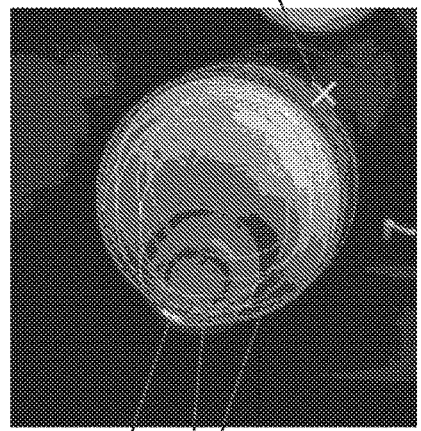
FIG. 9B, FIG. 9D, FIG. 9F and FIG. 9H show the selected tube top circles and other detected circle candidates in the ROI image patches shown at FIG. 9A, FIG. 9C, FIG. 9E and FIG. 9G, respectively, according to embodiments disclosed herein.
Figure 9A:
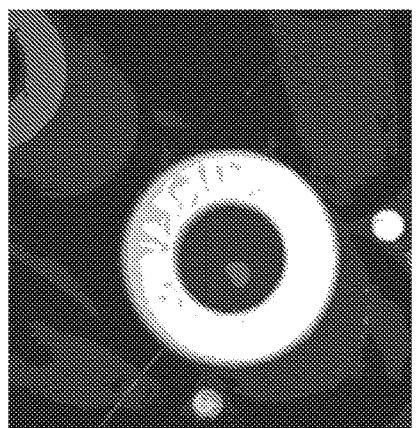
Figure 9B:
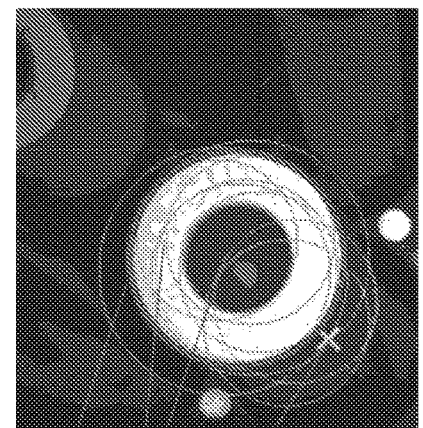
Figure 9E:
Figure 9F:
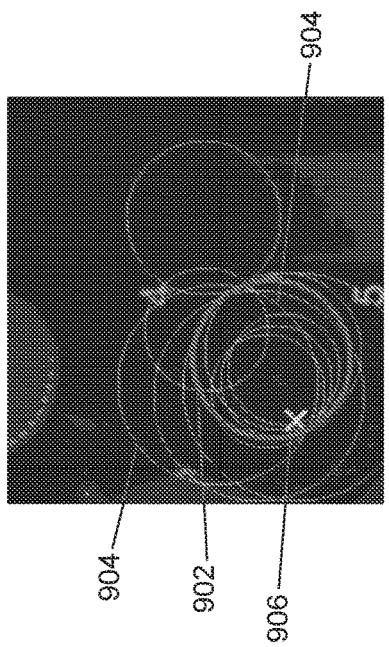
Figure 9G:
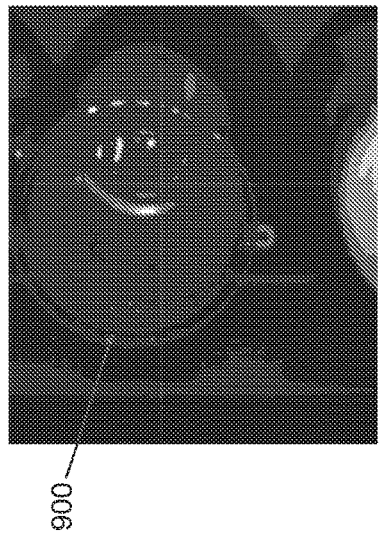
Figure 9H:
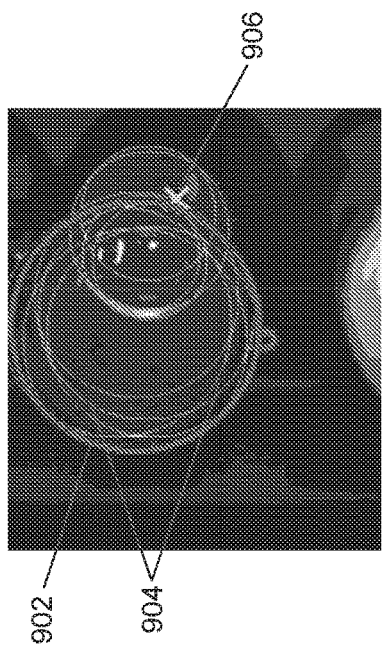
Figure 11A:
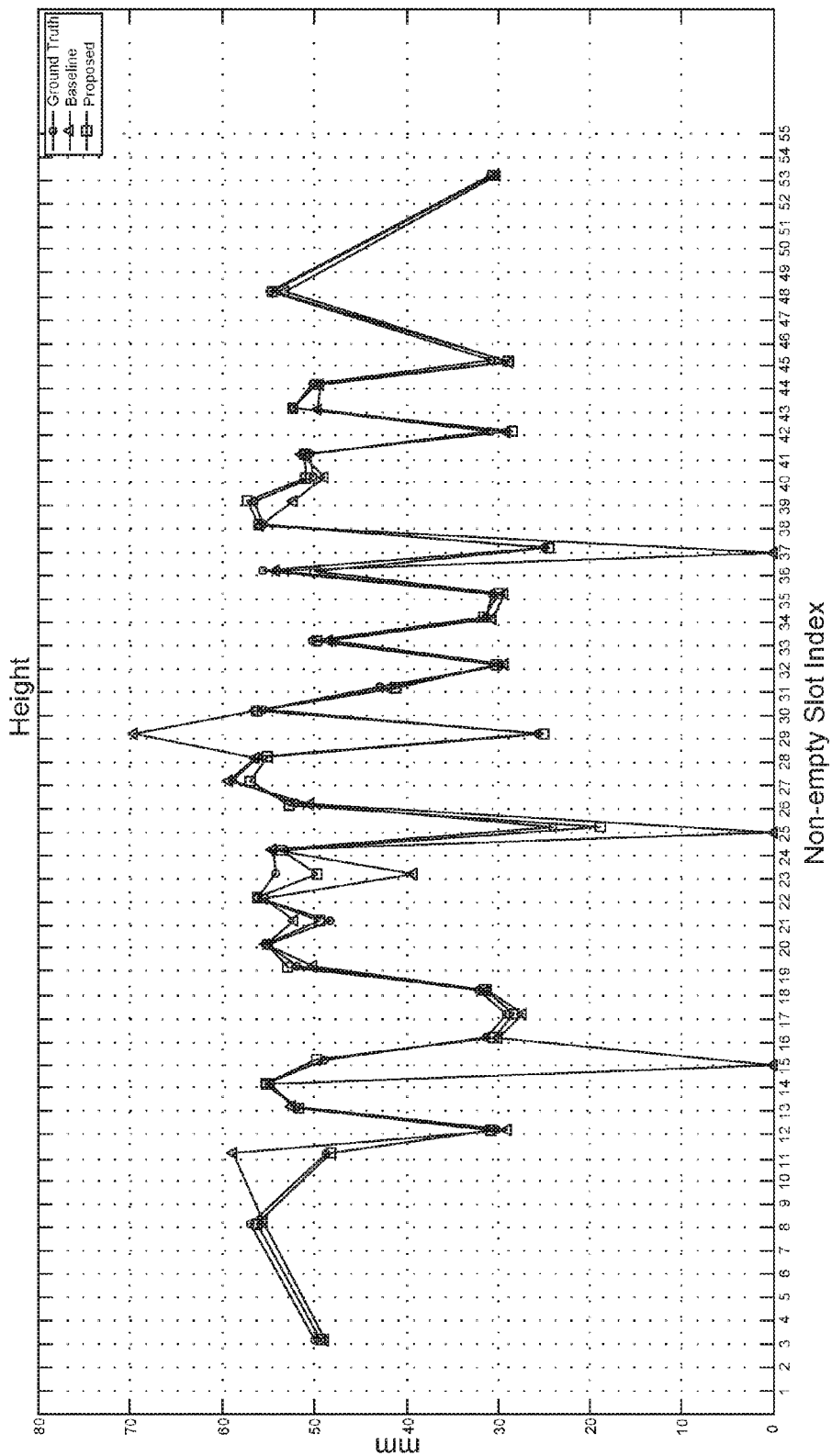
FIG. 11A through FIG. 11D are graphical illustrations showing results of tube top circle detection performed according embodiments disclosed herein.
Figure 11B:
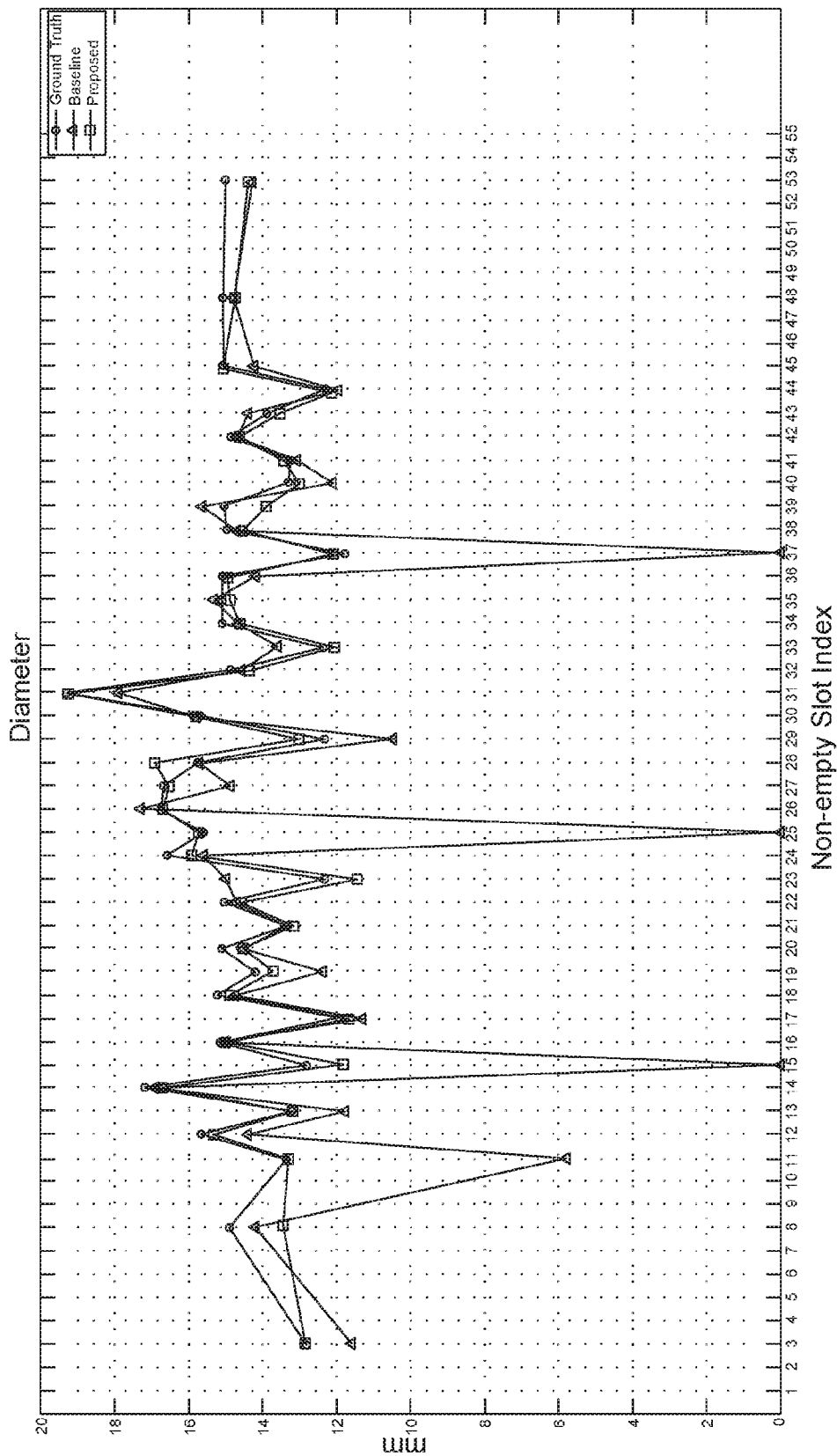
Figure 11C:
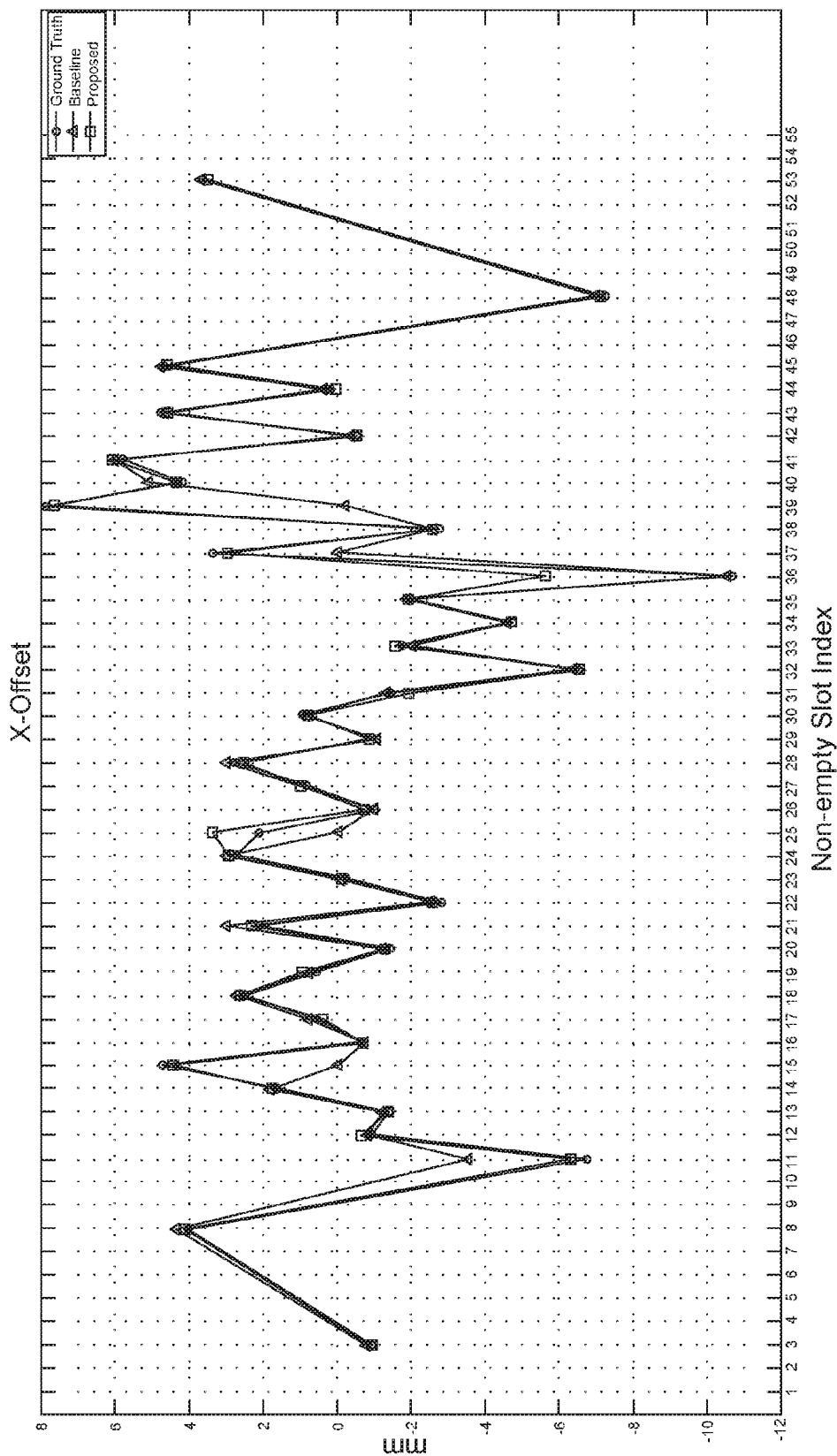
Figure 11D:
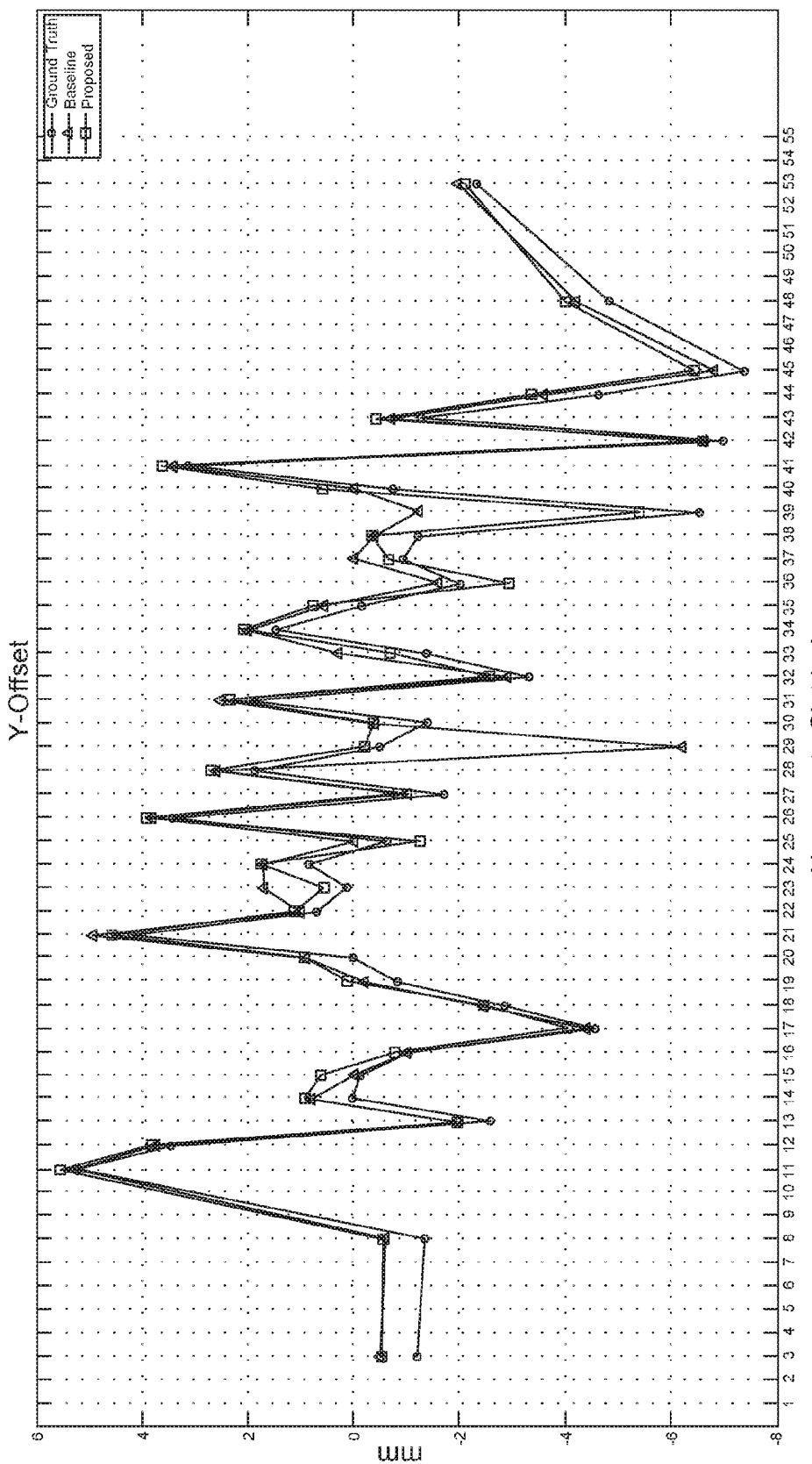

Embodiments described herein accurately detect tube top circles in images having multiple circles (e.g., circles within circles) by using a 3D Hough transform to construct 3D maps of the edge gradient magnitude maps to search circle centers and diameters simultaneously. FIG. 8 illustrates part of an exemplary 3D map construction according to embodiments disclosed herein. Given a set of edge points (e.g., edge point A shown in FIG. 8) and specular points 702 (shown in FIG. 7D) detected on the ROI, a 3D map 802 for 3D Hough Transform may be constructed. The 3D map 802 shown in FIG. 8 is a discrete 3-dimensional circle parameter space, where each location (x, y, d) corresponds to a specific circle parameter with center location (x, y) and diameter d. A processor, such as controller 220, may be used to construct the 3D map 302.

In some embodiments, an additional 2D map may be constructed for efficient optimal circle detection. The 2D map (not shown) is a discrete 2-dimensional parameter space where each location (x, y) corresponds to a specific circle center location. In some embodiments, extracted image patches include pixel resolutions of more than 250× 250 pixel$^2$ and tube diameters corresponding to about 70 pixels in the image. For these image patches, the 3D Hough transform space is large, but sparse, as there are typically only a few circles in the ROI. Embodiments may include image patches having different pixel resolutions and tube diameters corresponding to different amounts of pixels in the image. The additional 2D map is constructed via a 2D Hough transform and may be used to collect the accumulated edge magnitudes that contribute to each circle center for sorting and pre-filtering, preventing exhaustive sorting on the 3D Hough transform space. The 2D Hough transform space may be filled when the 3D Hough transform is performed. With this map, sparse locations may be targeted with a sufficient amount of accumulated edge magnitudes. Sorting may also be performed to target locations with higher accumulated edge magnitudes that are more likely to include the optimal tube top circle.

Referring back to the 3D construction, embodiments may include constructing a 3D map 802 based on any number of edge points along any number of edges in the ROI and the edge points (e.g., edge point A) from any number circles may contribute votes to different circle candidates along their edge gradient directions. To simplify explanation of the 3D construction process, however, FIG. 8 illustrates a part of the 3D construction based on a single edge point A along a single detected edge 804 of a circle.

A line $L_A$ may be determined through edge point A along its gradient direction. Points $(x_1^P, y_1^P), (x_2^P, y_2^P), (x_3^P, y_3^P)$, $(x_1^N, y_1^N), (x_2^N, y_2^N), (x_3^N, y_3^N)$ on the line $L_A$ that are equal to or within a predefined distance from the edge point A receive weighted votes. In the embodiment shown at FIG. 8, three points $(x_1^P, y_1^P), (x_2^P, y_2^P), (x_3^P, y_3^P)$, on the positive gradient side and three points $(x_1^N, y_1^N), (x_2^N, y_2^N), (x_3^N, y_3^N)$ on the negative gradient side are determined to be equal to or within a predefined distance from the edge point A. Embodiments may, however, determine any number of points (including zero points) to be equal to or within a predefined distance from an edge point. The weighted vote may be accumulated in both the 3D map 802 and the 2D map. For example, a processor, such as controller 220, may be used to accumulate weighted votes in the 3D map 802 and the 2D map from edge points in the edge gradient map along gradient directions of each of the edge points. As illustrated in FIG. 8, point A is an edge point and $L_A$ is the line along its gradient where its arrow shows the gradient direction. Points on the positive gradient side (e.g., $(x_1^P, y_1^P), (x_2^P, y_2^P), (x_3^P, y_3^P)$ . . . ) will receive a weighted vote $v^P$, while points on the negative gradient side (e.g., $(x_1^N, y_1^N), (x_2^N, y_2^N), (x_3^N, y_3^N)$ . . . ) receive a weighted vote $v^N$. A processor, such as controller 220, may be used to determine one or more locations in the 3D map 802 as a circle candidate when accumulated votes in the 3D map 802 are equal to or greater than a predetermined threshold.

True tube top circles are typically darker outside and brighter inside mainly due to the black tray surface at the background. Embodiments may therefore weigh circle candidates more heavily along positive gradient directions to accurately determine a tube top circle in an extracted ROI patch having one or more non-tube top circles (e.g., circular patterns of sample tubes from nearby slots, tube slots and tube label boundaries). For example, the value of the weighted votes $v^P$ and $v^N$ can be set to be proportional to the edge magnitude at the edge point A, where $v^P$ can be set to be larger than $v^N$ to favor points on the positive gradient side or vice versa. These votes will get accumulated in the 3D map based on the point location $(x_k, y_k)$ and the value $d_k$, (where k is an integer) which is twice of its distance to the edge point A. In other words, edge point A will contribute a vote $v^P$ to the 3D map at locations of $(x_1^P, y_1^P, d_1^P), (x_2^P, y_2^P, d_2^P), (x_3^P, y_3^P, d_3^P)$ . . . and a vote $v^N$ at locations $(x_1^N, y_1^N, d_1^N), (x_2^N, y_2^N, d_2^N), (x_3^N, y_3^N, d_3^N)$ . . . of the 3D map.

For circle candidates determined to include specular points 702, equal weights may be given on positive and negative gradient directions because both sides of specular points 702 are typically equally dark. For example, each specular point in the ROI also contributes votes $v_s^P$ and $v_s^N$ (where s is an integer) to the 3D map for points located on its gradient line. However, the votes for points on positive and negative gradient sides are set to be the same (i.e., $v_s^P = v_s^N$) in this embodiment as the gradient direction at a specular point is less reliable.

An optimal tube top circle may be selected by first identifying the location of edges with the highest accumulated votes in the 2D Hough map. The 2D map can be thought as an integral projection of the 3D map along its third dimension d. In practice, the 2D map may be more efficiently constructed using the votes each edge point or specular point contributes to the 3D map by ignoring the third parameter $d_k$. The 2D map serves as an efficient pre-screening map when we seek for the optimal parameter in the sparse 3D map. That is, the optimal parameter (x*, y*, d*) in the 3D map is more likely to have highly accumulated votes at (x*, y*) in the 2D map. Therefore, we can use the 2D map to filter out an entire row $\{(x_L, y_L, d)\}_{d=d_{min}}^{d_{max}}$ of the 3D map where the accumulated votes at $(x_L, y_L)$ is lower than a predefined threshold on the 2D map. Alternatively, we can use the accumulated votes in the 2D map to rank the locations of circle centers. The optimal circle center and diameter may then be determined in the 3D map according to the rank order of circle center locations in the 2D map.

The location of edges with the highest accumulated votes are identified in the 2D Hough map. For example, a processor may determine locations in the 2D map having accumulated votes larger than a first predetermined threshold. The corresponding 3D Hough map may then be traversed to determine whether the accumulated votes of each edge is sufficiently large to consider the edge as a circle candidate. That is, a processor may also determine the corresponding locations in the 3D map as circle candidates when accumulated votes at the locations in the 3D map are equal to or greater than a second predetermined threshold. In some embodiments, the first predetermined threshold may be equal to the second predetermined threshold. In other embodiments, the first predetermined threshold may have a value different from the second predetermined threshold. When it is determined that the accumulated votes are sufficiently large to consider the edge as a circle candidate, it may be determined whether the edge's center is close to an existing circle candidate's center and whether the areas of the two circle candidates have a sufficiently large overlap. If so, the circle candidate having the larger diameter is selected as the circle candidate. If the edge's center is not close to an existing circle candidate's center or the areas of the two circle candidates do not have a sufficiently large overlap, the edge is selected as the circle candidate and the circle is ranked in a circle candidate list according to its accumulated votes. This will effectively deal with the images including circles within circles.

The circle candidate having the greatest accumulated votes in the ranked list of circle candidates satisfying the physical tube geometry constraints may be selected, by a processor such as controller 220, as the target tube top circle. FIG. 9A, FIG. 9C, FIG. 9E and FIG. 9G show extracted ROI image patches each including a different target tube top circles 900. FIG. 9B, FIG. 9D, FIG. 9F and FIG. 9H are ROI image patches showing the selected tube top circles 902 and other circle candidates 904. As shown in FIG. 9B, FIG. 9D, FIG. 9F and FIG. 9H, selected tube top circles 902 correspond to the target tube top circles 900. Locations of the tube slot centers are indicted by markers 906.

FIG. 10A through FIG. 10D show sample images of a tube offset tool. To have a formal evaluation on the performance of tube top circle detection, a tube offset tool was created that glued various types of tubes in a randomly fixed tube center offsets as shown in FIG. 10. The ground truth of each tube's height, diameter, and center offset is measured with a robotic arm simulating a coordinate measuring machine CMM.

FIG. 11A through FIG. 11D are graphical illustrations showing results from methods and systems disclosed herein. By comparing a baseline implementation adapted from the conventional 2D Hough transform approach, significant improvement can be observed for the proposed approach as shown in 11A through FIG. 11D.

Figure 12:
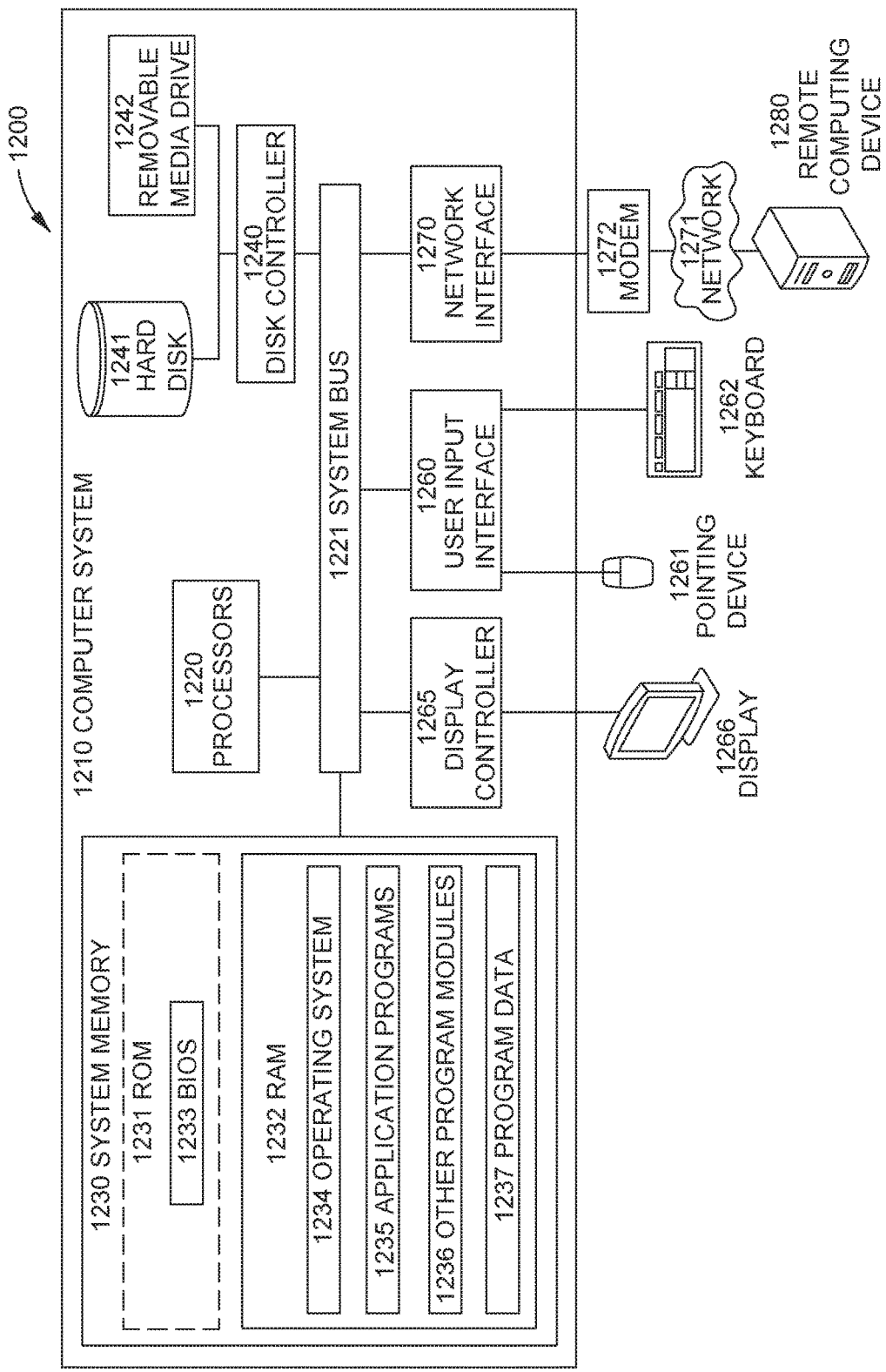
FIG. 12 illustrates an example of a computing environment within which embodiments of the invention may be implemented.

FIG. 12 illustrates an example of a computing environment 1200 within which embodiments of the invention may be implemented. Computing environment 1200 may be implemented as part of any component described herein. Computing environment 1200 may include computer system 1210, which is one example of a computing system upon which embodiments of the invention may be implemented. As shown in FIG. 12, the computer system 1210 may include a communication mechanism such as a bus 1221 or other communication mechanism for communicating information within the computer system 1210. The system 1210 further includes one or more processors 1220 coupled with the bus 1221 for processing the information. The processors 1220 may include one or more CPUs, GPUs, or any other processor known in the art.

The computer system 1210 also includes a system memory 1230 coupled to the bus 1221 for storing information and instructions to be executed by processors 1220. The system memory 1230 may include computer readable storage media in the form of volatile and/or nonvolatile memory, such as read only memory (ROM) 1231 and/or random access memory (RAM) 1232. The system memory RAM 1232 may include other dynamic storage device(s) (e.g., dynamic RAM, static RAM, and synchronous DRAM). The system memory ROM 1231 may include other static storage device(s) (e.g., programmable ROM, erasable PROM, and electrically erasable PROM). In addition, the system memory 1230 may be used for storing temporary variables or other intermediate information during the execution of instructions by the processors 1220. A basic input/output system (BIOS) 1233 containing the basic routines that help to transfer information between elements within computer system 1210, such as during start-up, may be stored in ROM 1231. RAM 1232 may contain data and/or program modules that are immediately accessible to and/or presently being operated on by the processors 1220. System memory 1230 may additionally include, for example, operating system 1234, application programs 1235, other program modules 1236 and program data 1237.

The computer system 1210 also includes a disk controller 1240 coupled to the bus 1221 to control one or more storage devices for storing information and instructions, such as a magnetic hard disk 1241 and a removable media drive 1242 (e.g., floppy disk drive, compact disc drive, tape drive, and/or solid state drive). The storage devices may be added to the computer system 1210 using an appropriate device interface (e.g., a small computer system interface (SCSI), integrated device electronics (IDE), Universal Serial Bus (USB), or FireWire).

The computer system 1210 may also include a display controller 1265 coupled to the bus 1221 to control a display or monitor 1266, such as a cathode ray tube (CRT) or liquid crystal display (LCD), for displaying information to a computer user. The computer system 1210 includes a user input interface 1260 and one or more input devices, such as a keyboard 1262 and a pointing device 1261, for interacting with a computer user and providing information to the processor 1220. The pointing device 1261, for example, may be a mouse, a trackball, or a pointing stick for communicating direction information and command selections to the processor 1220 and for controlling cursor movement on the display 1266. The display 1266 may provide a touch screen interface which allows input to supplement or replace the communication of direction information and command selections by the pointing device 1261.

The computer system 1210 may perform a portion or all of the processing steps of embodiments of the invention in response to the processors 1220 executing one or more sequences of one or more instructions contained in a memory, such as the system memory 1230. Such instructions may be read into the system memory 1230 from another computer readable medium, such as a hard disk 1241 or a removable media drive 1242. The hard disk 1241 may contain one or more data stores and data files used by embodiments of the present invention. Data store contents and data files may be encrypted to improve security. The processors 1220 may also be employed in a multi-processing arrangement to execute the one or more sequences of instructions contained in system memory 1230. In alternative embodiments, hard-wired circuitry may be used in place of or in combination with software instructions. Thus, embodiments are not limited to any specific combination of hardware circuitry and software.

As stated above, the computer system 1210 may include at least one computer readable medium or memory for holding instructions programmed according to embodiments of the invention and for containing data structures, tables, records, or other data described herein. The term "computer readable medium" as used herein refers to any non-transitory, tangible medium that participates in providing instructions to the processor 1220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1241 or removable media drive 1242. Non-limiting examples of volatile media include dynamic memory, such as system memory 1230. Non-limiting examples of transmission media include coaxial cables, copper wire, and fiber optics, including the wires that make up the bus 1221. Transmission media may also take the form of acoustic or light waves, such as those generated during radio wave and infrared data communications.

The computing environment 1200 may further include the computer system 1210 operating in a networked environment using logical connections to one or more remote computers, such as remote computer 1280. Remote computer 1280 may be a personal computer (laptop or desktop), a mobile device, a server, a router, a network PC, a peer device or other common network node, and typically includes many or all of the elements described above relative to computer 1210. When used in a networking environment, computer 1210 may include modem 1272 for establishing communications over a network 1271, such as the Internet. Modem 1272 may be connected to system bus 1221 via network interface 1270, or via another appropriate mechanism.

Network 1271 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1210 and other computers (e.g., remote computing system 1280). The network 1271 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1271.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation, a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface (UI) comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

A workflow processor, as used herein, processes data to determine tasks to add to, or remove from, a task list or modifies tasks incorporated on, or for incorporation on, a task list, as for example specified in a program(s). A task list is a list of tasks for performance by a worker, user of a device, or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and may include an event monitor. A processor in the workflow engine tracks which processes are running, for which patients, physicians, and what step needs to be executed next, according to a process definition and may include a procedure for notifying physicians of a task to be performed.

The system and processes of the figures presented herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of FIG. 12. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method of using image-based tube top circle detection, the method comprising:
receiving, from at least one camera, a series of images of a tray, the tray comprising a plurality of tube slots, each tube slot configured to receive a sample tube, the series of images of the tray being acquired via the at least one camera;
extracting, using a processor, a region of interest (ROI) patch from one of the series of images, the ROI patch comprising a target tube top circle and having boundaries constrained by two dimensional (2D) projections of a plurality of different types of tube top circle centers according to heights and diameters of a plurality of different types of sample tubes;
calculating, using the processor, an edge gradient magnitude map of the extracted ROI patch;
constructing, using the processor, a three dimensional (3D) map of a circle parameter space, where each location in the 3D map corresponds to a circle parameter having a center location and a diameter;
accumulating, using the processor, weighted votes in the 3D map from edge points in the edge gradient magnitude map along gradient directions of each of the edge points;
determining, using the processor, one or more locations in the 3D map as a circle candidate when the accumulated votes in the 3D map are equal to or greater than a predetermined threshold; and
selecting, using the processor, the determined circle candidate having the greatest accumulated votes as the target tube top circle.

2. The method of claim 1, wherein the tray is configured to fit within a portion of a drawer movable between an open position and a closed position and the image of the tray is acquired via the at least one camera as the drawer is moved between the open and the closed position.

3. The method of claim 1, further comprising:
predicting, using the processor, the two dimensional (2D) projection of each of the plurality of different types of tube top circle centers based on an intrinsic calibration of the at least one camera and an extrinsic pose with respect to a surface of the tray; and
constraining, using the processor, the boundaries of the ROI patch based on maximum and minimum settings of the plurality of different types of sample tubes, the maximum and minimum settings comprising: (i) a highest tube with a largest diameter; (ii) the highest tube with a smallest diameter; (iii) a shortest tube with the largest diameter; and (iv) the shortest tube with the smallest diameter.

4. The method of claim 1, further comprising determining, using the processor, a polygon that defines an area which the target tube top circle center is located based on the maximum and minimum settings.

5. The method of claim 1, wherein selecting the determined circle candidate having the greatest accumulated votes as the target tube top circle further comprises:
determining (i) whether the center of the circle is equal to or less than a predetermined distance threshold of a center of another circle candidate; and (ii) whether an area of the circle candidate and an area of the other circle candidate have an overlap equal to or greater than a predetermined overlap threshold;
when both (i) and (ii) are determined to be true, eliminating the circle candidate or the other circle candidate having the smaller diameter from being a circle candidate and if the diameters are equal, eliminating the circle candidate or the other circle candidate having the smaller amount of accumulated votes from being a circle candidate; and when either (i) or (ii) is determined to be false, ranking the circle candidate with other circle candidates according to the amount of accumulated votes.

6. The method of claim 1, wherein accumulating the weighted votes in the 3D map from the edge points in the edge gradient magnitude map along the gradient directions of each edge points further comprises:
determining a line intersecting each edge point along the gradient directions of each edge point; and
assigning one or more of the weighted votes to points on the line that are equal to or within a predefined distance from each edge point.

7. The method of claim 6, wherein accumulating the weighted votes in the 3D map from the edge points in the edge gradient magnitude map along the gradient directions of each edge points further comprises assigning greater weight to votes for points along positive gradient directions of each edge point than votes for points along negative gradient directions of each edge point.

8. The method of claim 1, further comprising:
determining, using the processor, specular points in the ROI patch,
assigning, using the processor, a first weight to votes along positive gradient directions of each specular point and assigning a second weight to votes along negative gradient directions of each specular point, wherein the first weight and the second weight are equal; and
accumulating, using the processor, the votes in the 3D map from the specular points along the positive gradient directions of each specular point and the negative gradient directions of each specular point.

9. The method of claim 1, further comprising:
constructing, using the processor, a 2D map of the circle center parameter space, each location of the 2D map corresponding to a circle center location;
determining, using the processor, accumulated weighted votes for the 2D map from edge points in the edge gradient magnitude map along the gradient directions of each edge point; and
filtering out, using the processor, one or more rows in the 3D map when the accumulated votes at corresponding locations on the 2D map are lower than a predefined threshold.

10. The method of claim 1, further comprising:
constructing, using the processor, a 2D map of the circle center parameter space, each location of the 2D map corresponding to a specific center location;
determining, using the processor, accumulated weighted votes for the 2D map from edge points in the edge gradient magnitude map along the gradient directions of each edge point; and
ranking, using the processor, the 2D circle center locations in the 2D map according to accumulated weighted votes in the 2D map.

11. A vision system for use in an in vitro diagnostics environment comprising:
a tray comprising a plurality of tube slots arranged in a matrix of rows and columns, each tube slot configured to receive a sample tube;
a surface configured to receive the tray;
at least one camera configured to capture a series of images of the tray; and
a processor configured to:
extract a region of interest (ROI) patch from one of the series of images, the ROI patch comprising a target tube top circle and having boundaries constrained by two dimensional (2D) projections of a plurality of different types of tube top circle centers according to heights and diameters of a plurality different types of sample tubes;
calculate an edge gradient magnitude map of the extracted ROI patch;
construct a three dimensional (3D) map of a circle parameter space where each location in the 3D map corresponds to a circle parameter having a center location and a diameter;
accumulate weighted votes in the 3D map from edge points in the edge gradient magnitude map along gradient directions of each of the edge points;
determine one or more locations in the 3D map as a circle candidate when accumulated votes at the one or more locations in the 3D map is equal to or greater than a predetermined threshold; and
select the determined circle candidate having the greatest accumulated votes as the target tube top circle.

12. The system of claim 11, wherein the surface comprises a portion of a drawer movable between an open and a closed position and the image of the tray is acquired via the at least one camera as the drawer is moved between the open position and the closed position.

13. The system of claim 11, wherein the processor is further configured to:
predict the two dimensional (2D) projection of each of the plurality of different types of tube top circle centers based on an intrinsic calibration of the at least one camera and an extrinsic pose with respect to a surface of the tray; and
constrain the boundaries of the ROI patch based on maximum and minimum settings of the plurality of different types of sample tubes, the maximum and minimum settings comprising: (i) a highest tube with a largest diameter; (ii) the highest tube with a smallest diameter; (iii) a shortest tube with the largest diameter; and (iv) the shortest tube with the smallest diameter.

14. The system of claim 11, wherein the processor is further configured to determine a polygon that defines an area which the target tube top circle center is located based on the maximum and minimum settings.

15. The system of claim 11, wherein the processor is further configured to select the determined circle candidate having the greatest accumulated votes as the target tube top circle by:
determining (i) whether the center of the circle is equal to or less than a predetermined distance threshold of a center of another circle candidate; and (ii) whether an area of the circle candidate and an area of the other circle candidate have an overlap equal to or greater than a predetermined overlap threshold;
when both (i) and (ii) are determined to be true, eliminating the circle candidate or the other circle candidate having the smaller diameter from being a circle candidate and if the diameters are equal, eliminating the circle candidate or the other circle candidate having the smaller amount of accumulated votes from being a circle candidate; and
when either (i) or (ii) is determined to be false, ranking the circle candidate with other circle candidates according to accumulated votes.

16. The system of claim 11, wherein the processor is further configured to accumulate the weighted votes in the 3D map from the edge points in the edge magnitude map along the gradient directions of each edge point by:

determining a line intersecting each edge point along the gradient direction of each edge point; and assigning one or more weighted votes to points on the line that are equal to or within a predefined distance from each edge point.

17. The system of claim 16, wherein the processor is further configured to accumulate the weighted votes in the 3D map from edge points in the edge gradient magnitude map along the gradient directions of each edge point by assigning greater weight to votes along positive gradient directions of each edge point than votes along negative gradient directions of each edge point.

18. The system of claim 11, wherein the processor is further configured to:

determine specular points in the extracted ROI patch, assign a first weight to votes along positive gradient directions of each specular point and assign a second weight to votes along negative gradient directions of each specular point, wherein the first weight and the second weight are equal; and accumulate the votes in the 3D map from the specular points along the positive gradient directions of each specular point and the negative gradient directions of each specular point.

19. The system of claim 11, wherein the processor is further configured to:

construct a 2D map of the circle center parameter space having one or more, each of the one or more locations of the 2D map corresponding to a circle center location; and determine accumulated weighted votes in the 2D map from edge points in the edge gradient magnitude map along the gradient directions of each edge point; and filter out one or more rows in the 3D map when the accumulated votes at corresponding locations on the 2D map is lower than a predefined threshold.

20. The system of claim 11, wherein the processor is further configured to:

construct a 2D map of the circle center parameter space having on or more locations, each of the one or more locations of the 2D map corresponding to a specific circle center location;

determine accumulated weighted votes on the 2D map from edge points in the edge gradient magnitude map along gradient directions of each edge point; and rank the one or more locations in the 2D map according to accumulated votes in the 2D map.

21. A method of using image-based tube top circle detection, the method comprising:

receiving, from at least one camera, a series of images of a tray, the tray comprising a plurality of tube slots, each tube slot configured to receive a sample tube, the series of images of the tray being acquired via the at least one camera;

extracting, using a processor, a region of interest (ROI) patch from one of the series of images, the ROI patch comprising a target tube top circle and having boundaries constrained by two dimensional (2D) projections of a plurality of different types of tube top circle centers according to heights and diameters of a plurality different types of sample tubes;

calculating, using the processor, an edge gradient magnitude map of the extracted ROI patch;

constructing, by the processor, a 2D map and a three dimensional (3D) map of a circle parameter space, each location in the 2D map corresponding to a circle center location and each location in the 3D map corresponding to a circle center and a diameter parameter;

accumulating, using the processor, weighted votes in the 2D map and in the 3D map based on edge points in the edge gradient magnitude map along gradient directions of each edge point;

determining, using the processor, one or more locations in the 2D map having accumulated votes larger than a first predetermined threshold;

determining, using the processor, the corresponding locations in the 3D map as circle candidates when accumulated votes at the corresponding locations in the 3D map are equal to or greater than a second predetermined threshold; and selecting, using the processor, the determined circle candidate having the greatest accumulated votes as the target tube top circle.

22. The method of claim 21, wherein the tray is configured to fit within a portion of a drawer movable between an open position and a closed position and the image of the tray is acquired via the at least one camera as the drawer is moved between the open and the closed position.

* * * * *